US012773254B2

(12) United States Patent
Kennedy et al.

(10) Patent No.: US 12,773,254 B2
(45) Date of Patent: *Oct. 27, 2026

(54) LOW-POWER TISSUE SEALING DEVICE AND METHOD

(71) Applicant: BOLDER SURGICAL, LLC, Marlborough, MA (US)

(72) Inventors: Jenifer Kennedy, Boulder, CO (US); Dale Schmaltz, Fort Collins, CO (US); David Schechter, Boulder, CO (US); Joel Helfer, Cheshire, CT (US); David Ross, Orange, CT (US)

(73) Assignee: Bolder Surgical, LLC, Marlborough, MA (US)

( * ) Notice: Subject to any disclaimer, the term of this patent is extended or adjusted under 35 U.S.C. 154(b) by 171 days.

This patent is subject to a terminal disclaimer.

(21) Appl. No.: 18/646,759

(22) Filed: Apr. 26, 2024

(65) Prior Publication Data

US 2024/0366284 A1 Nov. 7, 2024

Related U.S. Application Data

(63) Continuation of application No. 17/866,320, filed on Jul. 15, 2022, now Pat. No. 11,998,260, which is a (Continued)

(51) Int. Cl.
*A61B 18/12* (2006.01)
*A61B 18/14* (2006.01)
(Continued)

(52) U.S. Cl.
CPC ...... *A61B 18/1233* (2013.01); *A61B 18/1206* (2013.01); *A61B 18/1445* (2013.01);
(Continued)

(58) Field of Classification Search
CPC ........... A61B 2018/00619; A61B 2018/00625; A61B 2018/0063; A61B 2018/0225;
(Continued)

(56) References Cited

U.S. PATENT DOCUMENTS

| | | | |
|---|---|---|---|
| 4,001,745 | A | 1/1977 | Goodman et al. |
| 4,438,766 | A | 3/1984 | Bowers et al. |

(Continued)

FOREIGN PATENT DOCUMENTS

| | | |
|---|---|---|
| DE | 29805534 | 8/1998 |
| EP | 0640317 | 3/1995 |

(Continued)

OTHER PUBLICATIONS

Final Office Action for U.S. Appl. No. 13/153,513 dated Oct. 6, 2014.

(Continued)

*Primary Examiner* — Eun Hwa Kim
(74) *Attorney, Agent, or Firm* — Vista IP Law Group, LLP

(57) ABSTRACT

An electrosurgical instrument has a power supply operatively coupled to an end effector. The end effector has a pair of jaws for effectuating an action on tissue positioned therebetween. The power supply is configured to input a first signal and a second signal to a buck-boost converter. The buck-boost converter is configured to transmit an output to an H-bridge circuit. The H-bridge circuit is configured to pass a signal to a resonant LC transformer circuit. The power supply is configured to transmit a power signal. The pair of jaws are operatively coupled to the power supply to receive the power signal, the power having no more than 80 Volts RMS, and less than 2 Amps RMS. The power is configured to seal the tissue positioned between the pair of jaws in 3 seconds or less.

13 Claims, 17 Drawing Sheets

Related U.S. Application Data continuation of application No. 16/026,738, filed on Jul. 3, 2018, now Pat. No. 11,399,884, which is a continuation of application No. 14/990,584, filed on Jan. 7, 2016, now Pat. No. 10,166,064, which is a continuation of application No. 14/824,607, filed on Aug. 12, 2015, now Pat. No. 9,265,561, which is a continuation of application No. 13/153,513, filed on Jun. 6, 2011, now Pat. No. 9,144,455.

(60) Provisional application No. 61/352,114, filed on Jun. 7, 2010.

(51) Int. Cl.
*A61B 17/00* (2006.01)
*A61B 18/00* (2006.01)

(52) U.S. Cl.
CPC .................... *A61B 18/1482* (2013.01); *A61B 2017/00141* (2013.01); *A61B 2018/00607* (2013.01); *A61B 2018/00619* (2013.01); *A61B 2018/0063* (2013.01); *A61B 2018/00642* (2013.01); *A61B 2018/00678* (2013.01); *A61B 2018/00702* (2013.01); *A61B 2018/00708* (2013.01); *A61B 2018/0072* (2013.01); *A61B 2018/00767* (2013.01); *A61B 2018/00875* (2013.01)

(58) Field of Classification Search
CPC ...... A61B 2018/146; A61B 2018/1462; A61B 2018/1442; A61B 2018/1445; A61B 2018/1447; A61B 18/085
See application file for complete search history.

(56) References Cited

U.S. PATENT DOCUMENTS 4,569,345 A 2/1986 Manes
4,574,801 A 3/1986 Manes
4,617,927 A 10/1986 Manes
4,658,819 A 4/1987 Harris et al.
4,658,820 A 4/1987 Klicek
4,850,353 A 7/1989 Stasz et al.
4,903,696 A 2/1990 Stasz et al.
4,905,691 A 3/1990 Rydell
4,936,281 A 6/1990 Stasz
4,961,739 A 10/1990 Thompson
5,007,908 A 4/1991 Rydell
5,013,312 A 5/1991 Parins et al.
5,047,026 A 9/1991 Rydell
5,222,971 A 6/1993 Willard et al.
5,258,006 A 11/1993 Rydell et al.
5,282,799 A 2/1994 Rydell
5,304,190 A 4/1994 Reckelhoff et al.
5,342,359 A 8/1994 Rydell
5,342,381 A 8/1994 Tidemand
5,352,222 A 10/1994 Rydell
5,356,408 A 10/1994 Rydell
5,403,312 A 4/1995 Yates et al.
5,441,516 A 8/1995 Wang et al.
5,445,638 A 8/1995 Rydell et al.
5,447,513 A 9/1995 Davison et al.
5,449,372 A 9/1995 Schmaltz et al.
5,458,598 A 10/1995 Feinberg et al.
5,462,546 A 10/1995 Rydell
5,484,409 A 1/1996 Atkinson et al.
5,484,435 A 1/1996 Fleenor et al.
5,496,317 A 3/1996 Goble et al.
5,514,134 A 5/1996 Rydell et al.
5,540,684 A 7/1996 Hassler, Jr.
5,540,685 A 7/1996 Parins et al.
5,571,100 A 11/1996 Goble et al.
5,573,424 A 11/1996 Poppe
5,575,789 A 11/1996 Bell et al.
5,584,872 A 12/1996 LaFontaine et al.
5,599,344 A 2/1997 Paterson
5,599,350 A 2/1997 Schulze et al.
5,603,711 A 2/1997 Parins et al.
5,611,798 A 3/1997 Eggers
5,624,452 A 4/1997 Yates
5,637,111 A 6/1997 Sutcu et al.
5,647,869 A 7/1997 Goble et al.
5,666,035 A 9/1997 Basire et al.
5,667,480 A 9/1997 Knight et al.
5,669,907 A 9/1997 Plaft et al.
5,674,220 A 10/1997 Fox et al.
5,688,270 A 11/1997 Yates et al.
5,693,051 A 12/1997 Schulze et al.
5,709,680 A 1/1998 Yates et al.
5,716,366 A 2/1998 Yates
5,722,934 A 3/1998 Knight et al.
5,725,479 A 3/1998 Knight et al.
5,735,848 A 4/1998 Yates et al.
5,735,849 A 4/1998 Baden et al.
5,738,648 A 4/1998 Lands et al.
5,743,906 A 4/1998 Parins et al.
5,766,170 A 6/1998 Eggers
5,769,849 A 6/1998 Eggers
5,776,128 A 7/1998 Eggers
5,776,130 A 7/1998 Buysse et al.
H1745 H 8/1998 Paraschac et al.
5,797,938 A 8/1998 Paraschac et al.
5,807,392 A 9/1998 Eggers
5,807,393 A 9/1998 Williamson, IV et al.
5,810,805 A 9/1998 Sutcu et al.
5,810,808 A 9/1998 Eggers
5,810,811 A 9/1998 Yates et al.
5,817,093 A 10/1998 Williamson, IV et al.
5,827,271 A 10/1998 Buysse et al.
5,833,690 A 11/1998 Yates et al.
5,860,975 A 1/1999 Goble et al.
5,876,401 A 3/1999 Schulze et al.
5,891,141 A 4/1999 Rydell
5,891,142 A 4/1999 Eggers et al.
5,902,301 A 5/1999 Olig
5,902,328 A 5/1999 LaFontaine et al.
5,908,420 A 6/1999 Parins et al.
5,911,719 A 6/1999 Eggers
5,921,984 A 7/1999 Sutcu et al.
5,928,135 A 7/1999 Knight et al.
5,928,138 A 7/1999 Knight et al.
6,024,741 A 2/2000 Williamson, IV et al.
6,024,744 A 2/2000 Kese et al.
6,033,399 A * 3/2000 Gines ........................ H03L 5/02
606/50
6,039,733 A 3/2000 Buysse et al.
6,050,996 A 4/2000 Schmaltz et al.
D424,694 S 5/2000 Tetzlaff et al.
D425,201 S 5/2000 Tetzlaff et al.
6,063,086 A 5/2000 Benecke et al.
RE36,795 E 7/2000 Rydell
6,093,186 A 7/2000 Goble
6,096,037 A 8/2000 Mulier et al.
6,096,058 A 8/2000 Boche
6,102,909 A 8/2000 Chen et al.
6,110,171 A 8/2000 Rydell
6,113,598 A * 9/2000 Baker ................ A61B 18/1445
606/51
6,117,152 A 9/2000 Huitema
6,126,675 A 10/2000 Shchervinsky et al.
6,132,429 A 10/2000 Baker
6,165,175 A 12/2000 Wampler et al.
6,168,594 B1 1/2001 LaFontaine et al.
6,174,309 B1 1/2001 Wrubkewski et al.
6,179,834 B1 1/2001 Buysse et al.
6,187,003 B1 2/2001 Buysse et al.
6,190,383 B1 2/2001 Schmaltz
6,190,386 B1 2/2001 Rydell
6,193,653 B1 2/2001 Evans et al.
6,206,823 B1 3/2001 Kolata et al.
6,206,878 B1 3/2001 Bishop et al.
6,228,080 B1 5/2001 Gines

(56) References Cited

U.S. PATENT DOCUMENTS

| | | | |
|---|---|---|---|
| 6,238,387 | B1 | 5/2001 | Miller, III |
| 6,277,117 | B1 | 8/2001 | Tetzlaff et al. |
| 6,293,945 | B1 | 9/2001 | Parins et al. |
| D449,886 | S | 10/2001 | Tetzlaff et al. |
| 6,296,640 | B1 | 10/2001 | Wampler et al. |
| 6,352,536 | B1 | 3/2002 | Buysse et al. |
| 6,358,249 | B1 | 3/2002 | Chen et al. |
| 6,361,534 | B1 | 3/2002 | Chen et al. |
| 6,364,879 | B1 | 4/2002 | Chen et al. |
| 6,398,779 | B1 | 6/2002 | Buysse et al. |
| 6,419,675 | B1 | 7/2002 | Gallo, Sr. |
| 6,436,096 | B1 | 8/2002 | Hareyama |
| 6,440,130 | B1 | 8/2002 | Mulier et al. |
| 6,443,952 | B1 | 9/2002 | Mulier et al. |
| 6,443,970 | B1 | 9/2002 | Schulze et al. |
| 6,458,128 | B1 | 10/2002 | Schulze |
| 6,458,130 | B1 | 10/2002 | Frazier et al. |
| 6,464,702 | B2 | 10/2002 | Schulze et al. |
| 6,464,704 | B2 | 10/2002 | Schmaltz et al. |
| 6,468,275 | B1 | 10/2002 | Wampler et al. |
| 6,485,490 | B2 | 11/2002 | Wampler et al. |
| 6,511,476 | B2 | 1/2003 | Hareyama |
| 6,511,480 | B1 | 1/2003 | Tetzlaff et al. |
| 6,527,771 | B1 | 3/2003 | Weadock et al. |
| 6,547,786 | B1 | 4/2003 | Goble |
| 6,554,829 | B2 | 4/2003 | Schulze et al. |
| 6,572,615 | B2 | 6/2003 | Schulze et al. |
| 6,582,427 | B1 | 6/2003 | Goble et al. |
| 6,585,735 | B1 | 7/2003 | Frazier et al. |
| 6,592,582 | B2 | 7/2003 | Hess et al. |
| 6,592,604 | B2 | 7/2003 | Hess et al. |
| 6,607,529 | B1 | 8/2003 | Jones et al. |
| 6,610,060 | B2 | 8/2003 | Mulier et al. |
| 6,613,048 | B2 | 9/2003 | Mulier et al. |
| 6,616,656 | B2 | 9/2003 | Brommersma |
| 6,616,662 | B2 | 9/2003 | Scholer et al. |
| 6,620,161 | B2 | 9/2003 | Schulze et al. |
| 6,623,482 | B2 | 9/2003 | Pendekanti et al. |
| 6,652,521 | B2 | 11/2003 | Schulze |
| 6,656,176 | B2 | 12/2003 | Hess et al. |
| 6,667,685 | B2 | 12/2003 | Wasaki et al. |
| 6,679,892 | B2 | 1/2004 | Guido et al. |
| 6,682,528 | B2 | 1/2004 | Frazier et al. |
| 6,695,840 | B2 | 2/2004 | Schulze |
| 6,726,686 | B2 | 4/2004 | Buysse et al. |
| 6,736,813 | B2 | 5/2004 | Yamauchi et al. |
| 6,740,102 | B2 | 5/2004 | Hess et al. |
| 6,743,229 | B2 | 6/2004 | Buysse et al. |
| 6,755,827 | B2 | 6/2004 | Mulier et al. |
| 6,770,072 | B1 | 8/2004 | Truckai et al. |
| 6,773,409 | B2 | 8/2004 | Truckai et al. |
| 6,773,435 | B2 | 8/2004 | Schulze et al. |
| 6,776,780 | B2 | 8/2004 | Mulier et al. |
| 6,790,217 | B2 | 9/2004 | Schulze et al. |
| 6,796,981 | B2 | 9/2004 | Wham et al. |
| 6,832,998 | B2 | 12/2004 | Goble |
| 6,835,195 | B2 | 12/2004 | Schulze et al. |
| 6,843,789 | B2 | 1/2005 | Goble |
| 6,855,142 | B2 | 2/2005 | Harano et al. |
| 6,887,240 | B1 | 5/2005 | Lands et al. |
| 6,905,497 | B2 | 6/2005 | Truckai et al. |
| 6,923,805 | B1 | 8/2005 | LaFontaine et al. |
| 6,926,716 | B2 | 8/2005 | Baker et al. |
| 6,929,641 | B2 | 8/2005 | Goble et al. |
| 6,929,644 | B2 | 8/2005 | Truckai et al. |
| 6,942,662 | B2 | 9/2005 | Goble et al. |
| 6,960,209 | B2 | 11/2005 | Clague et al. |
| 6,966,907 | B2 | 11/2005 | Goble |
| 6,966,909 | B2 | 11/2005 | Marshall et al. |
| 6,984,231 | B2 | 1/2006 | Goble et al. |
| 7,001,382 | B2 | 2/2006 | Gallo, Sr. |
| 7,011,657 | B2 | 3/2006 | Truckai et al. |
| 7,033,356 | B2 | 4/2006 | Latterell et al. |
| D521,641 | S | 5/2006 | Reschke et al. |
| 7,041,102 | B2 | 5/2006 | Truckai et al. |
| 7,063,699 | B2 | 6/2006 | Hess et al. |
| 7,070,597 | B2 | 7/2006 | Truckai et al. |
| 7,083,619 | B2 | 8/2006 | Truckai et al. |
| 7,087,054 | B2 | 8/2006 | Truckai et al. |
| 7,112,201 | B2 | 9/2006 | Truckai et al. |
| 7,118,570 | B2 | 10/2006 | Tetzlaff et al. |
| 7,125,409 | B2 | 10/2006 | Truckai et al. |
| 7,131,970 | B2 | 11/2006 | Moses et al. |
| 7,137,980 | B2 | 11/2006 | Buysse et al. |
| 7,147,637 | B2 | 12/2006 | Goble |
| 7,150,748 | B2 | 12/2006 | Ebbutt et al. |
| 7,153,300 | B2 | 12/2006 | Goble |
| D535,396 | S | 1/2007 | Reschke et al. |
| 7,156,842 | B2 | 1/2007 | Sartor et al. |
| 7,156,844 | B2 | 1/2007 | Reschke et al. |
| 7,169,146 | B2 | 1/2007 | Truckai et al. |
| 7,179,258 | B2 | 2/2007 | Buysse et al. |
| 7,186,253 | B2 | 3/2007 | Truckai et al. |
| 7,189,231 | B2 | 3/2007 | Clague et al. |
| 7,189,233 | B2 | 3/2007 | Truckai et al. |
| 7,204,835 | B2 | 4/2007 | Latterell et al. |
| 7,211,084 | B2 | 5/2007 | Goble et al. |
| 7,214,224 | B2 | 5/2007 | Goble |
| 7,220,260 | B2 | 5/2007 | Fleming et al. |
| 7,235,072 | B2 | 6/2007 | Sartor et al. |
| 7,241,296 | B2 | 7/2007 | Buysse et al. |
| 7,244,257 | B2 | 7/2007 | Podhajsky et al. |
| 7,255,696 | B2 | 8/2007 | Goble et al. |
| 7,261,724 | B2 | 8/2007 | Molitor et al. |
| 7,267,677 | B2 | 9/2007 | Johnson et al. |
| 7,288,098 | B2 | 10/2007 | Huitema et al. |
| 7,297,149 | B2 | 11/2007 | Vitali et al. |
| 7,303,557 | B2 | 12/2007 | Wham et al. |
| 7,311,709 | B2 | 12/2007 | Truckai et al. |
| 7,322,975 | B2 | 1/2008 | Goble et al. |
| 7,329,256 | B2 | 2/2008 | Johnson et al. |
| 7,354,440 | B2 | 4/2008 | Truckai et al. |
| 7,364,577 | B2 | 4/2008 | Wham et al. |
| 7,377,920 | B2 | 5/2008 | Buysse et al. |
| 7,381,209 | B2 | 6/2008 | Truckai et al. |
| 7,491,199 | B2 | 2/2009 | Goble |
| 7,510,556 | B2 | 3/2009 | Nguyen et al. |
| 7,513,898 | B2 | 4/2009 | Johnson et al. |
| 7,553,312 | B2 | 6/2009 | Tetzlaff et al. |
| 7,582,087 | B2 | 9/2009 | Tetzlaff et al. |
| 7,632,269 | B2 | 12/2009 | Truckai et al. |
| 7,648,499 | B2 | 1/2010 | Orszulak et al. |
| 7,717,910 | B2 | 5/2010 | Goble |
| 7,722,602 | B2 | 5/2010 | Mihori |
| 9,144,455 | B2 | 9/2015 | Kennedy et al. |
| 9,265,561 | B2 | 2/2016 | Kennedy et al. |
| 9,532,828 | B2 | 1/2017 | Condie et al. |
| 9,615,826 | B2 | 4/2017 | Shelton, IV et al. |
| 10,166,064 | B2 | 1/2019 | Kennedy et al. |
| 10,441,354 | B2 | 10/2019 | Govari et al. |
| 10,582,964 | B2 | 3/2020 | Weinberg et al. |
| 11,399,884 | B2 | 8/2022 | Kennedy et al. |
| 2001/0037110 | A1 | 11/2001 | Schmaltz et al. |
| 2002/0013583 | A1 | 1/2002 | Camran et al. |
| 2002/0052599 | A1 | 5/2002 | Goble |
| 2002/0082596 | A1 | 6/2002 | Buysse et al. |
| 2002/0173787 | A1 | 11/2002 | Buysse et al. |
| 2003/0014052 | A1 | 1/2003 | Buysse et al. |
| 2003/0014053 | A1 | 1/2003 | Nguyen et al. |
| 2003/0018332 | A1 | 1/2003 | Schmaltz et al. |
| 2003/0073987 | A1 | 4/2003 | Sakurai et al. |
| 2003/0109875 | A1 | 6/2003 | Tetzlaff et al. |
| 2003/0114874 | A1 | 6/2003 | Craig et al. |
| 2003/0139741 | A1 | 7/2003 | Goble et al. |
| 2003/0181910 | A1 | 9/2003 | Dycus et al. |
| 2003/0195544 | A1 | 10/2003 | Hess et al. |
| 2004/0006340 | A1 | 1/2004 | Latterell et al. |
| 2004/0015163 | A1 | 1/2004 | Buysse et al. |
| 2004/0092927 | A1 | 5/2004 | Podhajsky et al. |
| 2004/0097921 | A1 | 5/2004 | Hess et al. |
| 2004/0122423 | A1 | 6/2004 | Dycus et al. |
| 2004/0143263 | A1 | 7/2004 | Schechter et al. |
| 2004/0147925 | A1 | 7/2004 | Buysse et al. |
| 2004/0186492 | A1 | 9/2004 | Hess et al. |

(56) References Cited

U.S. PATENT DOCUMENTS

| | | | | |
|---|---|---|---|---|
| 2004/0225288 | A1 | 11/2004 | Buysse et al. | |
| 2004/0230262 | A1 | 11/2004 | Sartor et al. | |
| 2004/0249374 | A1 | 12/2004 | Tetzlaff et al. | |
| 2005/0010212 | A1 * | 1/2005 | McClurken | A61B 18/1442 606/51 |
| 2005/0101945 | A1 | 5/2005 | Sakurai et al. | |
| 2005/0101952 | A1 | 5/2005 | Lands et al. | |
| 2005/0113823 | A1 | 5/2005 | Reschke et al. | |
| 2005/0134324 | A1 | 6/2005 | Boyer et al. | |
| 2005/0137592 | A1 | 6/2005 | Nguyen et al. | |
| 2005/0203504 | A1 | 9/2005 | Wham et al. | |
| 2005/0203507 | A1 | 9/2005 | Truckai et al. | |
| 2005/0240179 | A1 | 10/2005 | Buysse et al. | |
| 2005/0261676 | A1 | 11/2005 | Hall et al. | |
| 2005/0261677 | A1 | 11/2005 | Hall et al. | |
| 2005/0267464 | A1 | 12/2005 | Truckai et al. | |
| 2006/0030848 | A1 | 2/2006 | Craig et al. | |
| 2006/0047275 | A1 | 3/2006 | Goble | |
| 2006/0224155 | A1 | 10/2006 | Schmaltz | |
| 2006/0235440 | A1 | 10/2006 | Huitema et al. | |
| 2006/0235441 | A1 | 10/2006 | Huitema et al. | |
| 2006/0235442 | A1 | 10/2006 | Huitema | |
| 2006/0235443 | A1 | 10/2006 | Huitema et al. | |
| 2006/0235444 | A1 | 10/2006 | Huitema et al. | |
| 2006/0235468 | A1 | 10/2006 | Huitema et al. | |
| 2006/0259036 | A1 | 11/2006 | Tetzlaff et al. | |
| 2006/0264929 | A1 | 11/2006 | Goble et al. | |
| 2006/0271042 | A1 | 11/2006 | Latterell et al. | |
| 2007/0016235 | A1 | 1/2007 | Tanaka et al. | |
| 2007/0038209 | A1 | 2/2007 | Buysse et al. | |
| 2007/0062017 | A1 | 3/2007 | Dycus et al. | |
| 2007/0093810 | A1 | 4/2007 | Sartor et al. | |
| 2007/0118163 | A1 | 5/2007 | Boudreaux et al. | |
| 2007/0142832 | A1 | 6/2007 | Sartor et al. | |
| 2007/0146113 | A1 | 6/2007 | Truckai et al. | |
| 2007/0149987 | A1 | 6/2007 | Wellman et al. | |
| 2007/0149998 | A1 | 6/2007 | Wicks et al. | |
| 2007/0149999 | A1 | 6/2007 | Szabo et al. | |
| 2007/0150002 | A1 | 6/2007 | Szabo et al. | |
| 2007/0156140 | A1 | 7/2007 | Baily | |
| 2007/0173803 | A1 | 7/2007 | Wham et al. | |
| 2007/0173804 | A1 | 7/2007 | Wham et al. | |
| 2007/0191712 | A1 | 8/2007 | Messerly et al. | |
| 2007/0203488 | A1 | 8/2007 | Fleming et al. | |
| 2007/0208339 | A1 | 9/2007 | Arts et al. | |
| 2007/0213712 | A1 | 9/2007 | Buysse et al. | |
| 2007/0219549 | A1 | 9/2007 | Marshall et al. | |
| 2007/0273340 | A1 | 11/2007 | Miller et al. | |
| 2007/0299439 | A1 | 12/2007 | Latterell et al. | |
| 2008/0004639 | A1 | 1/2008 | Huitema et al. | |
| 2008/0009849 | A1 | 1/2008 | Goble et al. | |
| 2008/0009850 | A1 | 1/2008 | Goble et al. | |
| 2008/0015615 | A1 | 1/2008 | Molitor et al. | |
| 2008/0027465 | A1 | 1/2008 | Vitali et al. | |
| 2008/0027466 | A1 | 1/2008 | Vitali et al. | |
| 2008/0045942 | A1 | 2/2008 | Truckai et al. | |
| 2008/0077131 | A1 | 3/2008 | Yates et al. | |
| 2008/0132888 | A1 | 6/2008 | Iida et al. | |
| 2008/0132893 | A1 | 6/2008 | D'Amelio et al. | |
| 2008/0147062 | A1 | 6/2008 | Truckai et al. | |
| 2008/0188851 | A1 | 8/2008 | Truckai et al. | |
| 2008/0215051 | A1 | 9/2008 | Buysse et al. | |
| 2008/0287948 | A1 | 11/2008 | Newton et al. | |
| 2008/0294156 | A1 | 11/2008 | Newton et al. | |
| 2009/0012516 | A1 | 1/2009 | Curtis et al. | |
| 2009/0043304 | A1 | 2/2009 | Tetzlaff et al. | |
| 2009/0076506 | A1 | 3/2009 | Baker | |
| 2009/0093804 | A1 | 4/2009 | Newton | |
| 2009/0125014 | A1 | 5/2009 | Bouthillier et al. | |
| 2009/0171353 | A1 | 7/2009 | Johnson et al. | |
| 2009/0182323 | A1 | 7/2009 | Eder et al. | |
| 2009/0234355 | A1 | 9/2009 | Edwards et al. | |
| 2009/0248021 | A1 | 10/2009 | McKenna | |
| 2009/0259224 | A1 | 10/2009 | Wham et al. | |
| 2009/0306660 | A1 | 12/2009 | Johnson et al. | |
| 2009/0318915 | A1 | 12/2009 | Hosier et al. | |
| 2010/0042093 | A9 | 2/2010 | Wham et al. | |
| 2010/0082026 | A1 | 4/2010 | Curtis | |
| 2010/0114090 | A1 | 5/2010 | Hosier | |
| 2010/0130971 | A1 | 5/2010 | Baily | |
| 2010/0286685 | A1 | 11/2010 | Amoah et al. | |
| 2011/0184404 | A1 | 7/2011 | Walberg et al. | |
| 2011/0319882 | A1 | 12/2011 | Kennedy et al. | |

FOREIGN PATENT DOCUMENTS

| | | |
|---|---|---|
| EP | 0949886 | 10/1999 |
| EP | 1693015 | 8/2006 |
| EP | 2575660 | 4/2013 |
| JP | S61-222441 | 10/1986 |
| JP | 07-171163 | 7/1995 |
| JP | H11-5077857 | 7/1999 |
| JP | 2002325772 | 11/2002 |
| JP | 2005525861 | 9/2005 |
| JP | 2006167403 | 6/2006 |
| JP | 2007295980 | 9/2007 |
| JP | 2008539981 | 11/2008 |
| JP | 2016-112456 | 6/2016 |
| JP | 6309762 | 4/2018 |
| JP | 6363635 | 7/2018 |
| JP | 6483878 | 3/2019 |
| JP | 2019-084380 | 6/2019 |
| WO | WO 9710763 | 3/1997 |
| WO | WO 2004032776 | 4/2004 |
| WO | WO 2005004734 | 1/2005 |
| WO | WO 2010025815 | 3/2010 |
| WO | WO 2011156310 | 12/2011 |

OTHER PUBLICATIONS

Non-Final Office Action for U.S. Appl. No. 13/153,513 dated Mar. 13, 2015.

Non-Final Office Action for U.S. Appl. No. 13/153,513 dated May 22, 2014.

Notice of Allowance for U.S. Appl. No. 13/153,513 dated Jun. 2, 2015.

Wu, M.P., Ou C.S., Chen, S.L., Yen, E.Y.T., Rowbotham, R., "Complications and Recommended Practices for Electrosurgery in Laparoscopy". (2000), The American Journal of Surgery, vol. 179, pp. 67-73.

Amendment Response to NFOA for U.S. Appl. No. 13/153,513 dated Aug. 22, 2014.

Amendment Response to FOA for U.S. Appl. No. 13/153,513 dated Oct. 15, 2014.

Amendment Response to NFOA for U.S. Appl. No. 13/153,513 dated Apr. 27, 2015.

Moribayashi, Hirokazu, "Japanese Office Action re Application No. 2013-514276", Oct. 28, 2014, p. 9, Published in: JP.

Copenheaver, Blaine R, "International Search Report and Written Opinion re Application No. PCT/US11/57191", Feb. 14, 2012, p. 13, Published in: US.

Baharlou, S., "International Preliminary Report on Patentability re Application No. PCT/US2011/039365", Dec. 10, 2012, Published in: CH.

Copenheaver, Blaine R, "International Search Report and Written Opinion re Application No. PCT/US2011/039365", Nov. 16, 2011, p. 11, Published in: US.

J.S. Kennedy, et al, "Controlled Radio Frequency Vessel Sealing System of Surgical Applications", "Surgical Applications of Energy", Jan. 1998, p. 5, Publisher: SPIE Proceedings, Published in: US.

J.S. Kennedy, et al, "Large Vessel Ligation Using Bipolar Energy: A Chronic Animal Study and Histologic Evaluation", 1995, Page{s) 3, Publisher: Seventh International Meeting of the Society for Minimally Invasive Therapy, Published in: US.

J.S. Kennedy, et al, "High Burst Strength, Servoregulated, Bipolar Vessel Sealing", Jun. 1997, p. 6, Publisher: Joint Euro Asian Congress of Endoscopic Surgery, Published in: TR.

J.S. Kennedy, et al, "High Burst Strength. Feedback Controlled Bipolar Vessel Sealing", "Surgical Endoscopy—Ultrasound and Interventional Techniques", 1998, p. 3, Publisher: Springer-Verlag, Inc., Published in: US.

(56) References Cited

OTHER PUBLICATIONS

J.S. Kennedy, et al, “Recent Innovations in Bipolar Electrosurgery”, Jun. 1999, p. 5, Publisher: Isis Medical Media, Ltd., Published in: US.
J.S. Kennedy, et al, “Advances in Blood Vessel Sealing Technology and Methods”, Seventh International Meeting of the Society for Minimally Invasive Therapy, 1995.
J.S. Kennedy, et al, “Mechanisms of Electrosurgical Fusion for Large Vessel Hemostasis”, Seventh International Meeting of the Society for Minimally Invasive Therapy, 1995.
Notice of Allowance for U.S. Appl. No. 14/824,607 dated Oct. 8, 2015.
Moribayashi, Hirokazu, “Japanese Office Action re Application No. 2013514276”, Sep. 29, 2015, p. 7, Published in: JP.
Notice of Allowance for U.S. Appl. No. 14/990,584 dated Apr. 5, 2018.
Kim, Eun Hwa, “Office Action re U.S. Appl. No. 13/153,513”, filed Mar. 13, 2015, p. 46, Published in: US.
Kim, Eun Hwa, “Office Action re U.S. Appl. No. 13/153,513”, filed May 22, 2014, p. 79, Published in: US.
Kim, Eun Hwa, “Office Action re U.S. Appl. No. 13/153,513”, filed Oct. 6, 2014, p. 32, Published in: US.
Neugeboren, Craig, “Response to Office Action re U.S. Appl. No. 13/153,513”, filed Oct. 15, 2014, p. 13, Published in: US.
Schneider, Laura, “Response to Office Action re U.S. Appl. No. 13/153,513”, filed Apr. 27, 2015, p. 15, Published in: US.
Schneider, Laura, “Response to Office Action re U.S. Appl. No. 13/153,513”, filed Aug. 22, 2014, p. 17, Published in: US.
Neugeboren, Craig, “Response to Office Action re U.S. Appl. No. 13/153,513”, filed Apr. 23, 2014, p. 9, Published in: US.
Kim, Eun Hwa, “Office Action re U.S. Appl. No. 13/153,513”, filed Feb. 28, 2014, p. 9, Published in: US.
Schmidt, Matihias, “Extended European Search Report Re Application No. 11792980.2”, Apr. 7, 2017, p. 12, Published in: EP.
Riehl, Philippe, “Supplementary European Search Report Re Application No. 11835192”, Oct. 26, 2017, p. 2, Published in: EP.
Naito, Shintoku, “Japanese Office Action Re Application No. 2013-514276”, Oct. 3, 2017, p. 3, Published in: JP.
Takagi, Akira, “Japanese Office Action Re Application No. 2013-514276”,Feb. 7, 2017, p. 19, Published in: JP.
Nakamura, Kazuo, “Japanese Office Action Re Application No. 2016-015986”, Jan. 31, 2017, p. 8, Published in: JP.
Non-Final Office Action for U.S. Appl. No. 16/026,738 dated Dec. 21, 2021.
Amendment Response to NFOA for U.S. Appl. No. 16/026,738 dated Mar. 17, 2022.
Notice of Allowance for U.S. Appl. No. 16/026,738 dated Mar. 17, 2022.
Kazuo Nakamura, “Office Action re: Japanese Appln. No. 2018-016961,” Aug. 23, 2018, 14, JP.
Kenichi Managuchi, Patent Grant re: Appln. No. 2019-024359, Aug. 3, 2021, 2 pages, Japan Patent Office.
English Machine Translation of: Kenichi Managuchi, Patent Grant re: Appln. No. 2019-024359, Aug. 3, 2021, 2 pages, Japan Patent Office.
Kazuo Nakamura, “Office Action re: Appln. No. 2018-016961,” Aug. 28, 2018, 14 pages, published in Japan.
Kenichi, Yamaguchi, “Office Action re Japanese Application No. 2019-024359 and English Translation,” May 12, 2020, 8 pages.
European Patent Office, Examination Division, “Communication relating to the Patent Prosecution Highway (PPH) Pilot Program” re Application No. 11792980.2, May 20, 2020, 1 page. Published in: Europe.
Schmidt, Mathias, “Invitation Pursuant to Rule 137(4) re: Application No. 11792980.2,” Jun. 3, 2020, 5 pages, published in Europe.
Kazuo Nakamura, “Notice of Intention to Grant,” Jan. 15, 2019, 1 page, no translation available, published in Japan.
Foreign Exam Report for EP Patent Appln. No. 21 195 407.8 dated Nov. 27, 2025.

* cited by examiner

LOW-POWER TISSUE SEALING DEVICE AND METHOD

PRIORITY AND RELATED APPLICATIONS

This application is a continuation of U.S. patent application Ser. No. 17/866,320 filed on Jul. 15, 2022, and entitled "Low-Power Tissue Sealing Device and Method," which is a continuation of U.S. patent application Ser. No. 16/026,738 filed on Jul. 3, 2018, and entitled "Low Power Tissue Sealing Device and Method," now issued as U.S. Pat. No. 11,399,884, which is a continuation of U.S. patent application Ser. No. 14/990,584 filed on Jan. 7, 2016, and entitled "Low-Power Tissue Sealing Device and Method," now issued as U.S. Pat. No. 10,166,064, which is a continuation of U.S. patent application Ser. No. 14/824,607 filed on Aug. 12, 2015, and entitled "Low Power Tissue Sealing Device and Method," now issued as U.S. Pat. No. 9,265,561, which is a continuation of U.S. patent application Ser. No. 13/153,513 filed on Jun. 6, 2011, and entitled "Low Power Tissue Sealing Device and Method," now issued as U.S. Pat. No. 9,144,455, which claims the benefit of Provisional U.S. Application No. 61/352,114 filed on Jun. 7, 2010. The entire disclosures of which are hereby incorporated by reference into the present application in its entirety and for all proper purposes.

FIELD OF THE INVENTION

Aspects of the present invention relate to electrosurgical procedures, techniques, and devices that utilize radiofrequency energy to seal blood vessels during surgical procedures. In particular, and by no means of limitation, aspects of the present invention relate to devices and techniques for sealing precisely placed or otherwise sensitive or difficult to access blood vessels often found in micro-surgical procedures, difficult to access anatomy or general surgery in pediatric patients.

BACKGROUND

The use of electrosurgical energy in vessel sealing surgical procedures is common and has been used in conjunction with a variety of surgical techniques for many years. In general, electrosurgical devices used in vessel sealing rely on a combination of pressure and high frequency electric energy applied to biological tissue as a way to cut, coagulate, desiccate or seal tissue, for example, blood vessels. In the case of vessel sealing, the electrosurgical energy acts to create collagen melting and tissue fusion. Most RF surgical devices on the market today and described in the prior art have power delivery systems and end effectors that are sized to accommodate a wide range of situations, tissue thicknesses, tissue volume, and end effector bite sizes. In particular, vessel sealing technology has always relied upon the use of relatively high current settings and large end effector sizes to create a seal in varying surgical situations. No one has been able to produce a reliable vessel sealing instrument that operates at currents below 2 Amps.

For coagulation or blood vessel sealing with known devices, the average power density delivered by the end effector is typically reduced below the threshold of cutting. In some cases (e.g. a monopolar coagulation instrument) a modulated sine wave is used with the overall effect being a slower heating process which causes tissue to coagulate rather than burn and/or char to the point of cutting. In some simple dual function coagulation/cutting devices, a lower duty cycle is used for a coagulation mode and a higher duty cycle is used for a cutting mode with the same equipment. Coagulation and in particular vessel sealing techniques present unique challenges in electrosurgery.

While some modern electrosurgical generators provide modulated waveforms with power adjusted in real time based on changes of the tissue characteristics (e.g. impedance), none have been able to address the complexities and sensitivities that arise when dealing with blood vessels located in delicate surgical sites or other difficult to reach blood vessels. None of the prior art or products currently offered combine aspects of applied pressure, low-power energy delivery, waveform modulation, and instrument size/configuration to safely and effectively seal the blood vessels that are often presented in micro-surgical procedures, difficult to access anatomy or pediatric general surgery.

Recent advances in vessel sealing technology have specifically abandoned an attempt to address this specialized market and instead focus on larger devices and techniques for sealing larger vessels more commonly found in general surgery or on "one-size-fits all" devices. U.S. Pat. No. 5,827,271 describes how earlier attempts to seal vessels with electrosurgery were unsuccessful in part because they attempted to apply relatively low currents to the vessels. As a solution, the advances described in U.S. Pat. No. 5,827,271 relate to increasing the current applied to the blood vessel above a certain threshold. The prior art in this field is consistent in its recognition that a high current and high generator power output is required to seal vessels. None of the prior art addresses the unique circumstances presented with small caliber blood vessels that present during micro-surgical procedures, difficult to access anatomy or general surgery in pediatric patients. None of the art accounts for a technique or device that effectively and safely seals blood vessels with an instrument that is smaller in size (both in the shaft and entry point features) and configured to be more effective which working in smaller spaces and with smaller vessel calibers. None of the prior art recognizes the role of the surgical instrument size and end effector surface area in the development of effective vessel sealing techniques and energy delivery sequencing.

SUMMARY OF THE INVENTION

In one example, a surgical system for fusing is provided. The system has an electrosurgical generator capable of delivering electrosurgical power, a surgical instrument electrically connected to the electrosurgical generator and adapted to transfer the electrosurgical power from the electrosurgical generator to a distal end of the surgical instrument, and a power control circuit for controlling the delivery of radio frequency energy to the tissue in contact with the distal end of the surgical instrument. The surgical system is configured to: deliver the radio frequency energy at a non-pulsing power to the tissue for a period of time of 3 seconds or less. The non-pulsing power is held constant, the output current is held under 2 Amperes RMS, and the output voltage is held under 100 Volts RMS. The non-pulsing power further causes the tissue to begin to desiccate and to fuse within the period of time.

In another example, a power control system for delivering radio frequency energy to a surgical instrument is provided. The power control system has a power supply for delivering an output voltage and an output current to a distal end of the surgical instrument, a sensing circuit for detecting parameters indicative of an impedance of a tissue portion being fused, and a power sequencing module for automatically sequencing an electrosurgical power delivered to the surgical instrument. The power sequencing module is adapted to: apply non-pulsing power to the tissue portion for a period of time of 3 seconds or less. The period of time is measured from beginning an application of the non-pulsing power through the beginning of a desiccation of the tissue portion and through a drying out and the fusing of the tissue portion. The non-pulsing power is held constant, the output current is held under 2 Amperes RMS, and the output voltage is held under 100 Volts RMS.

In another example, a surgical system for fusing tissue is provided. The surgical system has an electrosurgical generator capable of delivering electrosurgical power; a surgical instrument electrically connected to the electrosurgical generator and adapted to transfer electrosurgical power from the electrosurgical generator to a distal end of the surgical instrument; and a power control circuit for controlling the delivery of radio frequency energy to the tissue through the distal end of the surgical instrument. The surgical system is configured to deliver a radio frequency energy to the tissue, the radio frequency energy having a non-pulsed power having an output current and an output voltage; and apply the non-pulsed power to the tissue for a period of time while the non-pulsed power is held constant, the output current is held under 2 Amperes RMS, and the output voltage is held under 100 Volts RMS. The period of time is measured from beginning the application of the non-pulsed power through fusing of the tissue, and the non-pulsed power causes the tissue to begin to desiccate within the period of time, wherein the period of time is 3 seconds or less.

In another example, a method of fusing tissue is provided. The method includes: providing a surgical system having an electrosurgical generator and a surgical instrument electrically connected to the electrosurgical generator and adapted to transfer electrosurgical power from the electrosurgical generator to a distal end of the surgical instrument. The method also includes delivering a radio frequency energy to the tissue, the radio frequency energy having a non-pulsed power having an output current and an output voltage; and applying the non-pulsed power to the tissue for a period of time while the non-pulsed power is held constant, the output current is held under 2 Amperes RMS, and the output voltage is held under 100 Volts RMS. The period of time is measured from the beginning of the application of the non-pulsed power and continues through fusing of the tissue. The non-pulsed power causes the tissue to begin to desiccate within the period of time, and the period of time is 3 seconds or less.

Other aspects will become apparent to one of skill in the art upon a review of the following drawings and detailed description.

BRIEF DESCRIPTION OF THE DRAWINGS

Various aspects, objects and advantages, and a more complete understanding of the present invention are apparent and more readily appreciated by reference to the following Detailed Description and to the appended claims when taken in conjunction with the accompanying Drawings, wherein:

Figure 1:
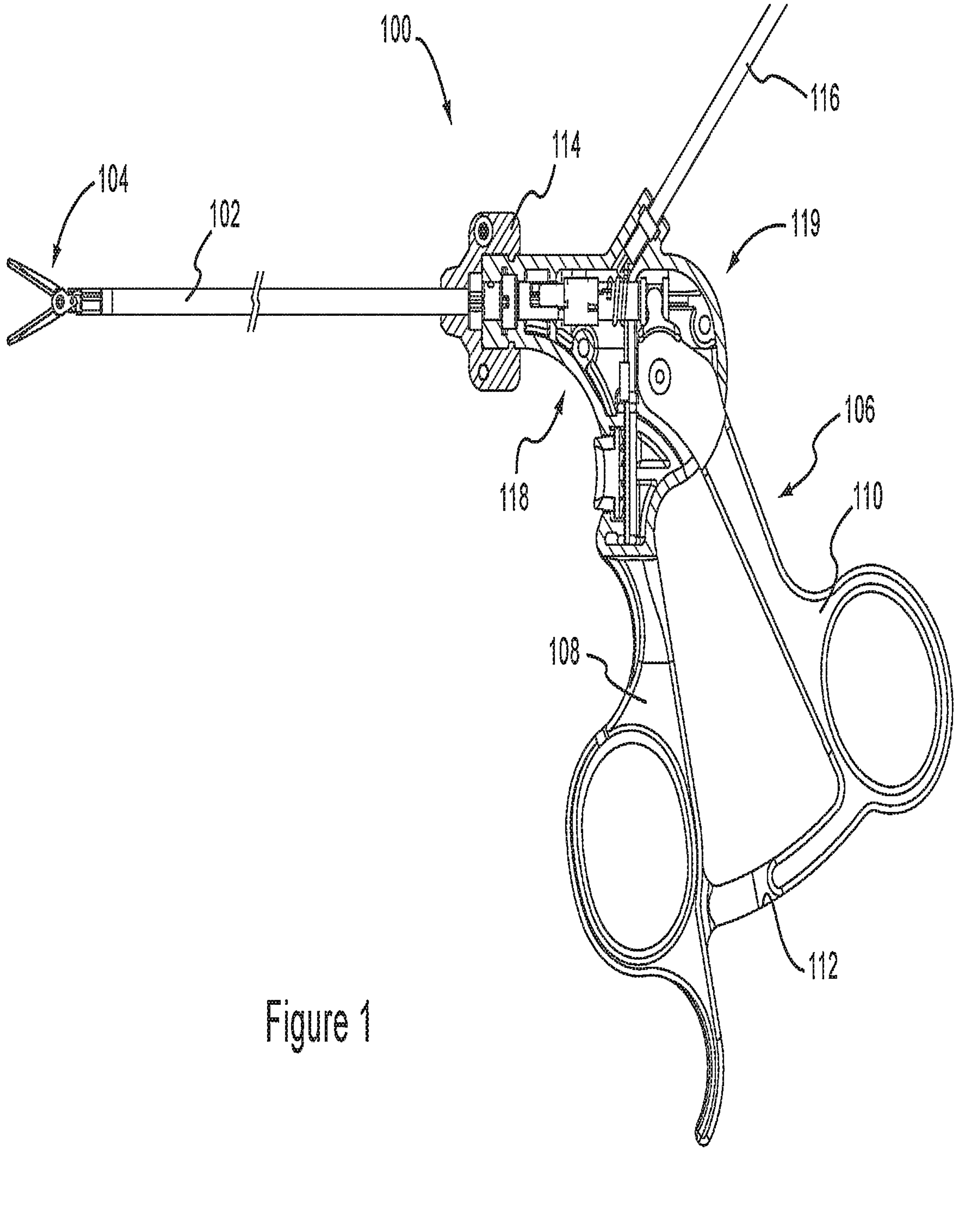
FIG. 1 is a side view of an electrosurgical instrument in accordance with aspects of the present invention.

Other aspects of devices and methods in accordance with the present invention will become known to those of skill in the art when read in conjunction with the following disclosure.

DETAILED DESCRIPTION

Throughout this specification references are made to the use of various materials, combinations, mechanical configurations, ranges and other aspects that may be used in various combinations to form one or more devices and methods in accordance with aspects of the present invention. It should be understood, both to one of skill in the art as well as the examining divisions in the United States Patent Office and Patent Offices throughout the world, that each of the lists of materials, examples, and other embodiments are included herein in order to teach one of skill in the art that they may be combined into various alternative embodiments, without requiring specific claim permutations of these individual features, and without departing from the spirit and scope of the invention. The claims as presented herein, as well as any potential future amendments to those claims, may include one or more combinations of these materials, ranges and other alternatives without departing from the spirit and scope of the invention described herein. In particular it is contemplated that one of skill in the art would recognize and find adequate support in the written description for any combination of the features disclosed herein, whether described in a single example or embodiment, or described in multiple and disjointed sections of the written description. The description of these various example and options is specifically drafted to comply with 35 U.S.C. § 112 of the United States Patent Laws, Article 123(2) of the European Patent Laws as well as other similar national country laws relating to the adequacy of the written description.

Aspects of a device constructed in accordance with the present invention generally pertain to a low-power vessel sealing system. Application of such devices have particular applicability in pediatric surgery and other situations where small caliber blood vessels may be encountered such as micro-surgery, difficult to access anatomy and all aspects of pediatric surgery. In addition, devices constructed in accordance with aspects of the present invention allow smaller profile instruments which in turn allow smaller incisions to be made during the associated surgical procedure. A system constructed in accordance with aspects of the present invention has as its major components an RF generator and a bipolar grasper/dissector/sealer instrument hand piece that plugs into the generator. Various power sequencing and control systems are incorporated into the generator and system logic that enable effective and safe vessel sealing capabilities at lower power outputs than is currently available or otherwise known in the art.

Features of an instrument and vessel sealing system constructed in accordance with aspects of the present invention may include one or more of the following, each of which is described in greater detail below.

Orientation and Operation of End Effectors

Aspects of a device constructed in accordance with the present invention include opposing electrically isolated end effector jaw members that provide energy delivery to tissue, such as a blood vessel, undergoing a surgical procedure. The jaws preferably open in a simultaneous dual action fashion, although other jaw movement dynamics are contemplated. The jaws are located on the distal end of a shaft that serves to maximize surgical site visibility in either open, endoscopic or laparoscopic procedures. The length of the instrument shaft may vary from 10 cm to 30 cm depending on the designed use. In one embodiment the instrument shaft may vary from 15 cm to 20 cm long. Furthermore, aspects of the present invention can be used in connection with both rigid shaft instruments and flexible shaft instruments such as might be found in steerable surgical systems or robotic surgical systems.

The size of the jaws may range from 1.0-3.5 mm in width and from 8.0-12.0 mm in length. The surfaces of the jaws may include one or more non-conductive elements that function to maintain electrical isolation between the jaw surfaces and keep the electrodes from shorting out. Preferably the jaws are designed to close in a parallel fashion, i.e. both jaw surfaces move in coordination with each other upon activation by a user. The instrument or end effector itself may or may not be built with a cutting instrument that serves to divide the tissue after sealing is accomplished.

In accordance with one aspect, an instrument end effector constructed in accordance with the present invention applies pressure to the tissue to be sealed in the range of 75-110 psi so that the tissue is adequately compressed prior to the sealing action taking place.

There is preferably limited play in the motion of the instrument handle. In one embodiment the ring handle design enables a close to 1-1 opening and closing of the jaws. A ratchet point may be incorporated into the handle assembly so that full jaw closure and the required pressure is applied prior to the sealing function.

Generator Capabilities and Function

With respect to the generator and electrical aspects of the present invention, features of a device constructed in accordance with aspects of the present invention include one or more of the following, each of which is described in greater detail below.

Energy is preferably applied to the tissue undergoing a surgical procedure at a constant power. The power delivery cycle may terminate when one or more of the following occurs: a) voltage reaches a maximum level not to exceed a set level such as 80 Volts RMS or 100 Volts RMS; b) impedance reaches a final value of between 180-350 ohms; and c) a maximum seal time of between 2 and 5 seconds is reached. In addition, voltage or current limits may be put in place that further confine the operational parameters of the power delivery system.

The generator has a power capability in the range of 25-35 Watts total power, but typical operation is preferably in the range of 8-15 Watts in order to control resolution and accuracy of the power output and to minimize the possibility of tissue charring and other damaging effects. A voltage limit incorporated into the generator operation minimizes the potential for tissue damage during a sealing procedure.

Maximum current delivery is under 2 Amps, and typical operation is in the range of 0.75-1.5 Amps. Maximum voltage of the system is 100 Volts RMS. The typical maximum voltage is in the range of 70-85 Volts RMS.

The above summary should be considered as one set of overall design parameters and not as any type of exclusive requirements for how a system or particular instrument is required to be designed in accordance with aspects of the present invention. In addition, any examples given throughout this specification, and any data or test results given throughout this specification, should not be used as evidence during prosecution of the claims herein of any intention by the applicant to limit the scope of any claims to those particular embodiments or examples. For example, maximum current delivery may be limited to under 1.5 Amps in one embodiment, under 1.0 amps in another embodiment and under 0.5 amps in yet another embodiment. In addition to the above, operation of the system may be in the range of 1.0-1.25 Amps. In another embodiment operation of the system may be in the range of 0.5 to 2 Amps. In other embodiments, maximum voltage of the system is 75 Volts RMS. In yet other embodiments maximum voltage of the system is 50 Volts RMS. In another embodiment the typical maximum voltage is in the range of 50-100 Volts RMS.

One of skill in the art would know to utilize various permutations of the described examples to arrive at the claim scope submitted below.

With reference to FIGS. 1-6, various drawings are shown that depict one example of a surgical instrument 100 that may be used in connection with aspects of the present invention. As shown in FIGS. 1-6, surgical instrument 100 is depicted as a forceps for use with a variety of laparoscopic and open procedures. As such, instrument 100 includes an elongated shaft 102 with an end effector 104 located at a distal end of the shaft 102. The shaft 102 and end effector 104 are coupled with a rotational element 114 that allows a user to rotate the shaft 102 and end effector 104 about the longitudinal axis of the shaft 102 thereby enabling various presentations of the end effector 104 within a surgical site.

Figure 2:
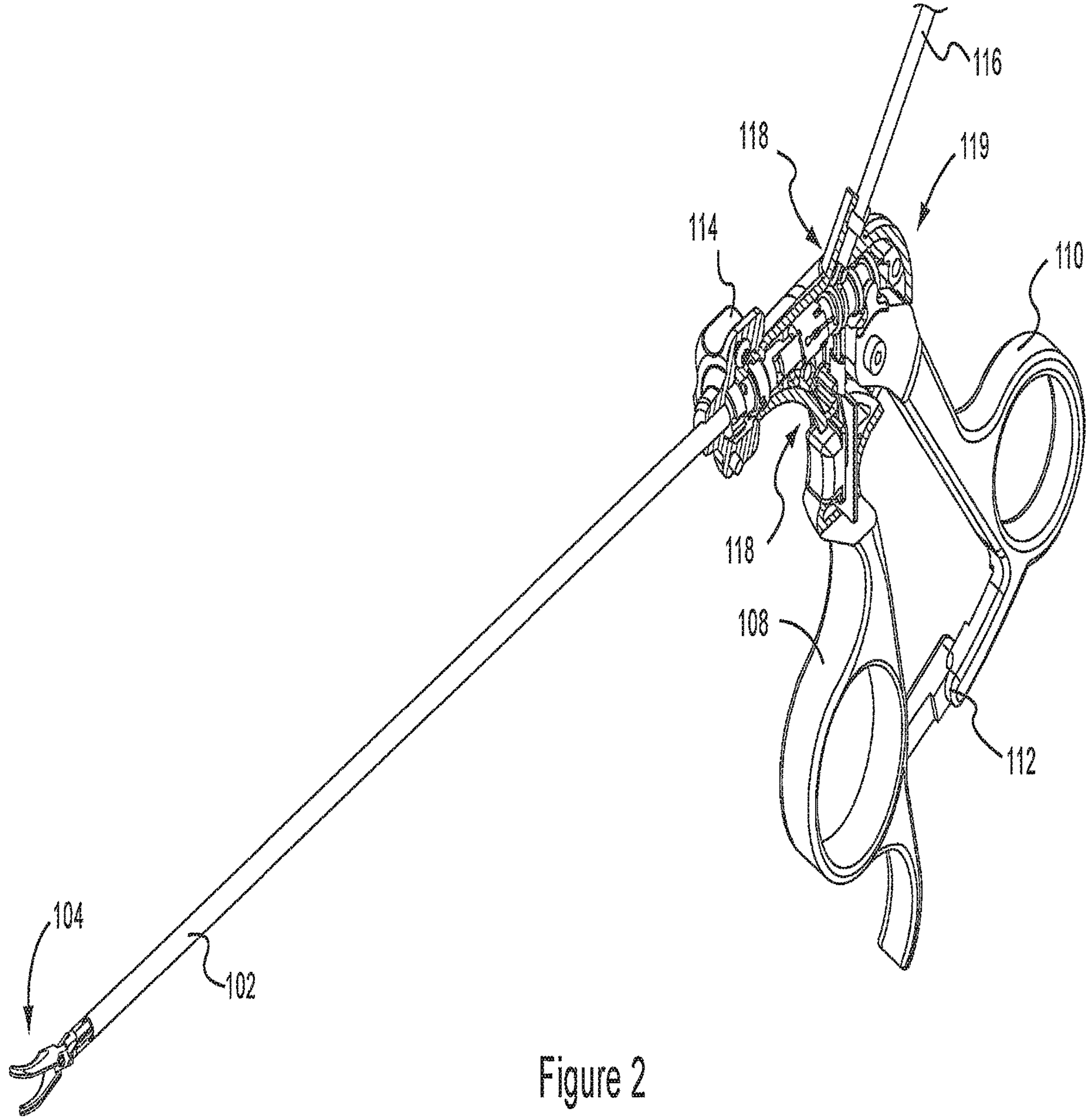
FIG. 2 is a perspective view of the electrosurgical instrument in FIG. 1.

A handle assembly 106 generally includes a stationary handle portion 108 and a thumb lever portion 110 that operate in conjunction with an actuation mechanism 119 to control the movement, physical engagement of and electrical engagement of the end effector 104. Each of the handle portion 108 and thumb lever portion 110 define an area for a user's fingers to engage the instrument and operate the handle assembly 106 in a scissor-like movement. As such, movement of the thumb lever portion 110 with respect to the handle portion 108 facilitates movement of the end effector from an open position to a closed position. In one embodiment the handle portion 108 and the thumb level portion 110 enable a single action movement of the end effector 104. A ratchet mechanism 112 is included for selectively locking the handle assembly 106 at a selected position during movement. In another embodiment, several ratchet stops are include so that a user can select a closure position and/or pressure applied by the end effector around a tissue sample. Electrical cable assembly 116 extends from a position in an electro-mechanical sub-assembly 118 and serves generally to connect the surgical instrument 100 to a power source, such as a radio frequency generator described below. Further details of the electrical cable assembly 116 are described below. FIG. 2 shows the surgical instrument 100 in a perspective view but generally illustrates the same features as those described in conjunction with FIG. 1 and that description is not repeated here.

Figure 3A:
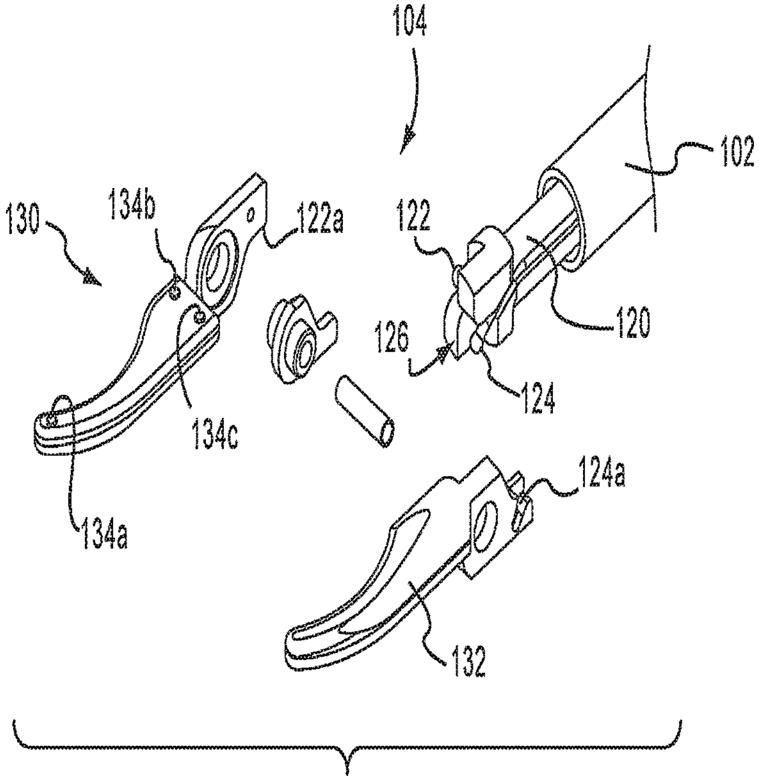
FIGS. 3A-3B are various views of an end effector constructed in accordance with aspects of the present invention.
Figure 3B:
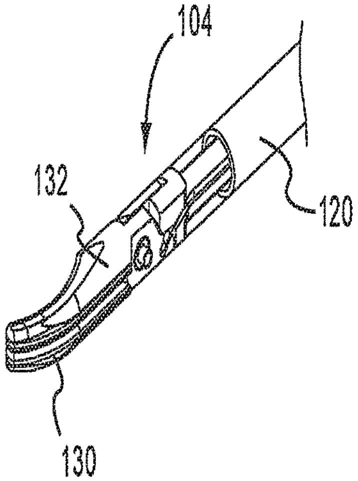
Figure 4:
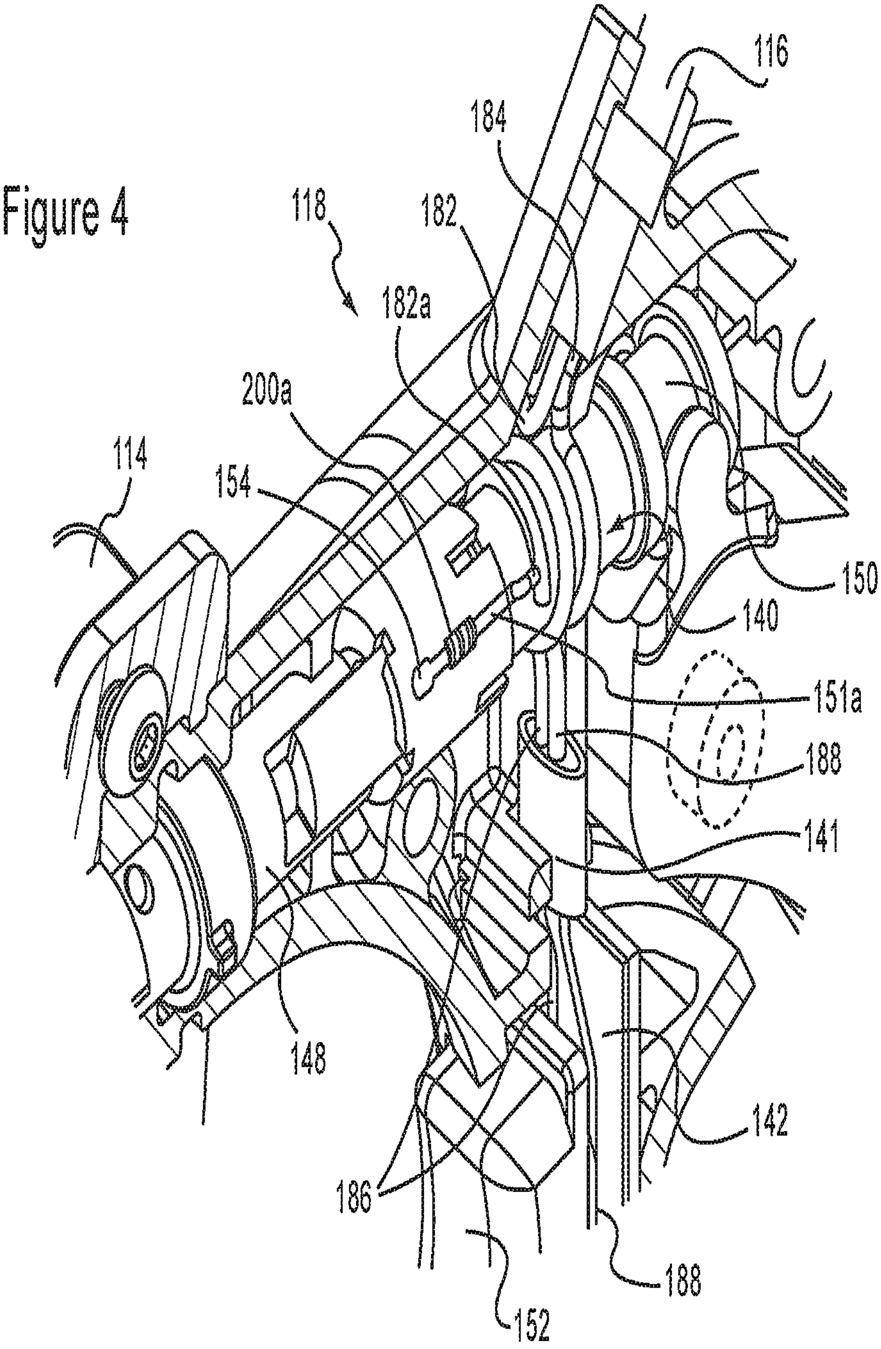
FIG. 4 is a close up of the mechanical and electrical engagement mechanisms of the electrosurgical instrument shown in FIG. 1.
Figure 5:
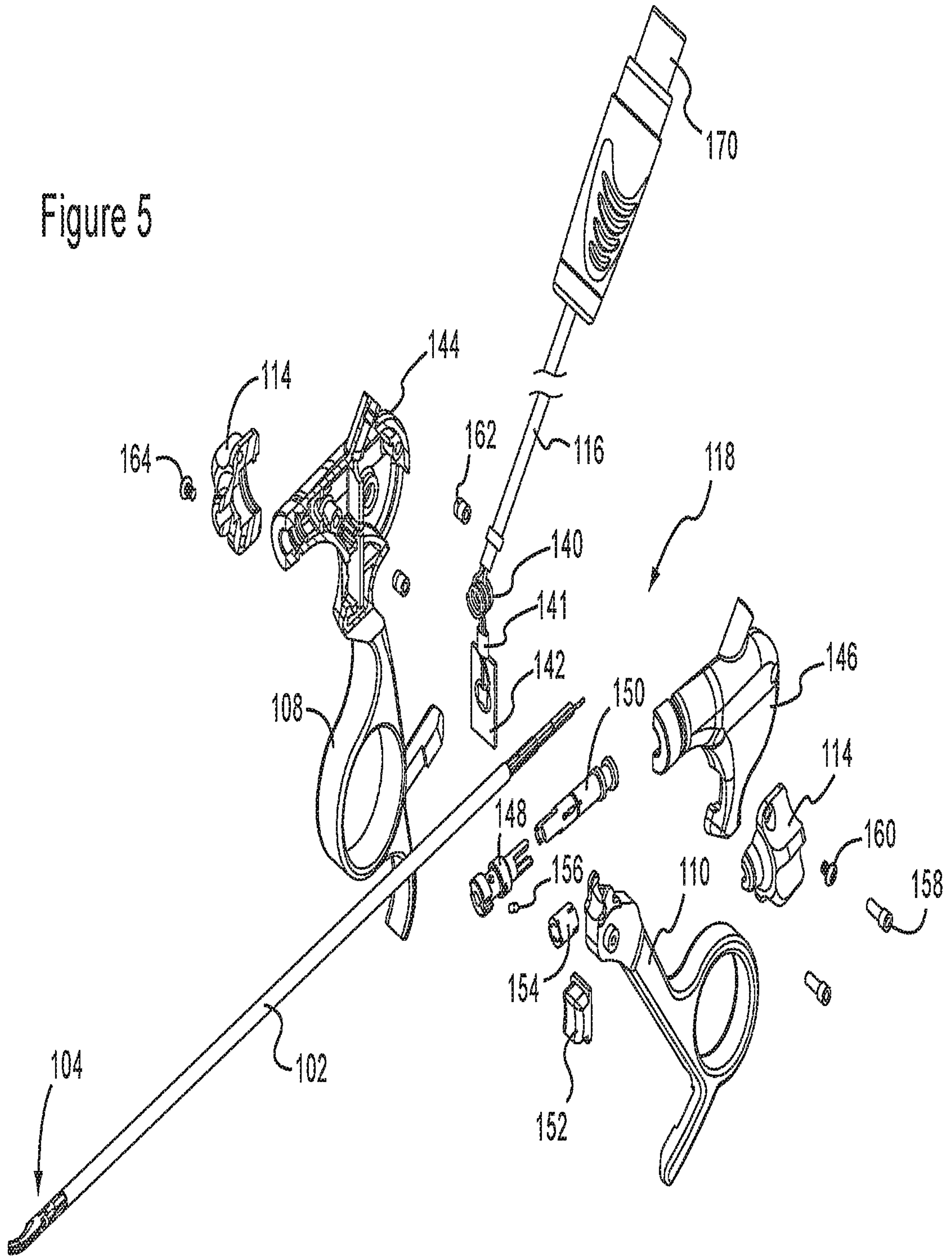
FIG. 5 is an exploded perspective view of the mechanisms shown in FIG. 4.

FIGS. 3A-3B show details of the end effector 104 of the surgical instrument 100. With continuing reference to FIGS. 3A-3B, the end effector 104 is shown in various perspectives and with varying detail. In the example of FIGS. 3A-3B, the end effector 104 is shown as a grasper/dissector, sealer combination. However, it is contemplated that various other instrument configurations may be employed without departing from the spirit and scope of the invention. For example, various alternate configurations of the grasper itself may be employed as well as different instruments, such as a dissector or cutter may be used in connection with the sealing aspects disclosed herein. The size and overall shape of the end effector may also be varied in accordance with other aspects of a device constructed in accordance with aspects of the present invention.

With respect to the grasper/dissector, sealer end effector 104 depicted in FIGS. 3A-3C, the end effector 104 includes opposing grasper portions 130 and 132 that are adapted to open and close as a result of the action of the handle assembly 108. Cables 122 and 124 engage with each of the grasper portions 130 and 132 and extend through the shaft 102 back to the handle assembly 108 where they engage with an electrical connection and linkage system 118. A tension block 126 secures the cables 122 and 124 at the distal end of the shaft 102 and provide a mechanism to couple each of the cables 122 and 124 with the grasper portions 130 and 132. In combination, this mechanical arrangement allows the grasper portions 130 and 132 to open and close when the thumb lever portion 110 is engaged by a user. As shown, the embodiment of the grasper/sealer 100 provides for both grasper portions 130 and 132 to move simultaneously in a single action motion when actuated by thumb lever portion 110.

With reference to FIGS. 4-6E, details of the electrical connection and linkage system 118 are shown. Overall, the electrical connection and linkage system 118 provides both a mechanical interface between the handle assembly 106 and the effected movement of the grasper portions 130 and 132, as well as an electrical interface between the cable assembly 116, which is connected to an electrosurgical power source, and the grasper portions 130 and 132. Actuation cables 151*a* and 151*b* extend from the jaw portions 130 and 132, are routed to the handle assembly 106 and are crimped and constrained to the cable collar 150. Electrical connections are made to the proximal ends of the actuation cables 151*a* and 151*b*. In some embodiments, the actuation cables 151*a* and 151*b* also conduct the current to the end effector 104 and to the tissue undergoing a procedure.

Actuation cables 151*a* and 151*b* route through the cable collar 150. Joined to each cable is a mechanically fastened ferrule crimp 200*a* and 200*b* near the proximal end of both cables, which allows the actuation cables to be pulled (to clamp/close the jaw portions 130 and 132) and pushed (to open the jaw portions 130 and 132). In the short section of actuation cables proximal to the ferrule crimp (shown as 151*a*), each of the two cables are electrically connected to the two poles of the electrosurgical power wires (182 and 184). This connection can be done with an additional electrical ferrule (crimped) or soldered. This is not a load bearing connection; simply electrical. The electrosurgical power wires wrap around the cable collar 150 to provide enough path length to allow the cable collar to rotate approximately one full rotation without causing undue strain on the power wires or electrical connections. The two poles of the electrosurgical trigger switch (188 and 186) form a closed loop in the flex circuit 142 (See FIG. 6B) when the dome contact is depressed by the trigger 152. The dome switch circuit activates the electrosurgical connection to actuation cables 151*a* and 151*b*, thereby conducting current down the length of the shaft to grasper portions 130 and 132. The rest state is an open loop when the trigger 152 is not depressed and there is no electrosurgical connection.

Figure 6A:
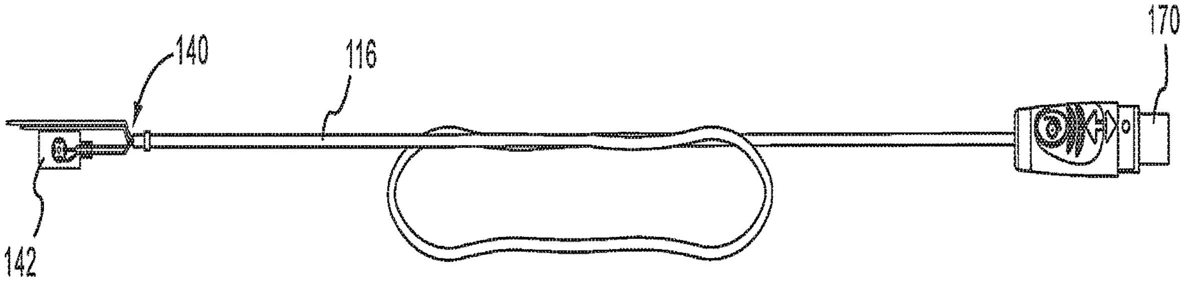
FIGS. 6A-6E show several views of an electrical cable and associated connection devices in accordance with aspects of the present invention.
Figure 6B:
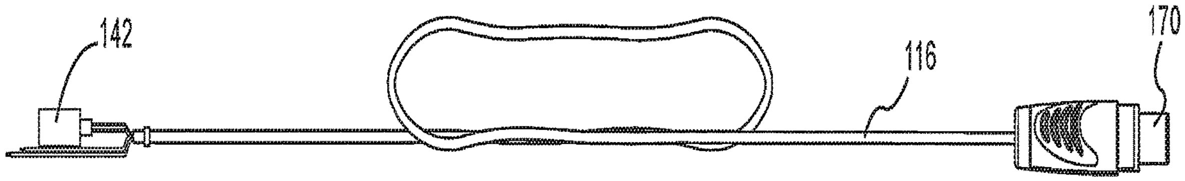
Figure 6B:
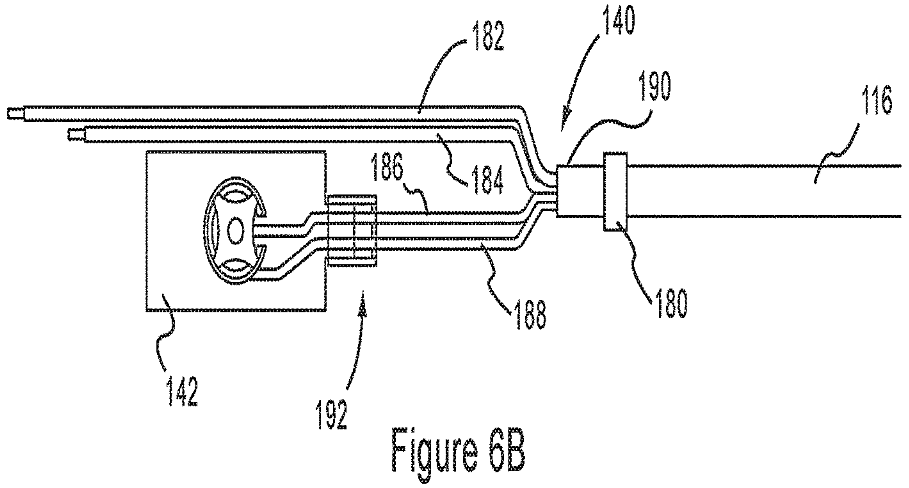

In accordance with proper functioning of the instrument and system is that the two poles remain electrically isolated at all times. Power wires 182 and 184, solder/crimp connections 182*a* and 182*b* (not shown), 151*a* and 151*b*, and jaw portions 130 and 132 have to remain isolated from each other. FIG. 6D shows how along the length of the Shaft 102 the actuation cables are isolated by an extrusion 210, and encapsulated on the outside by electrically isolating heat-shrink jacket 212.

Figure 6C:
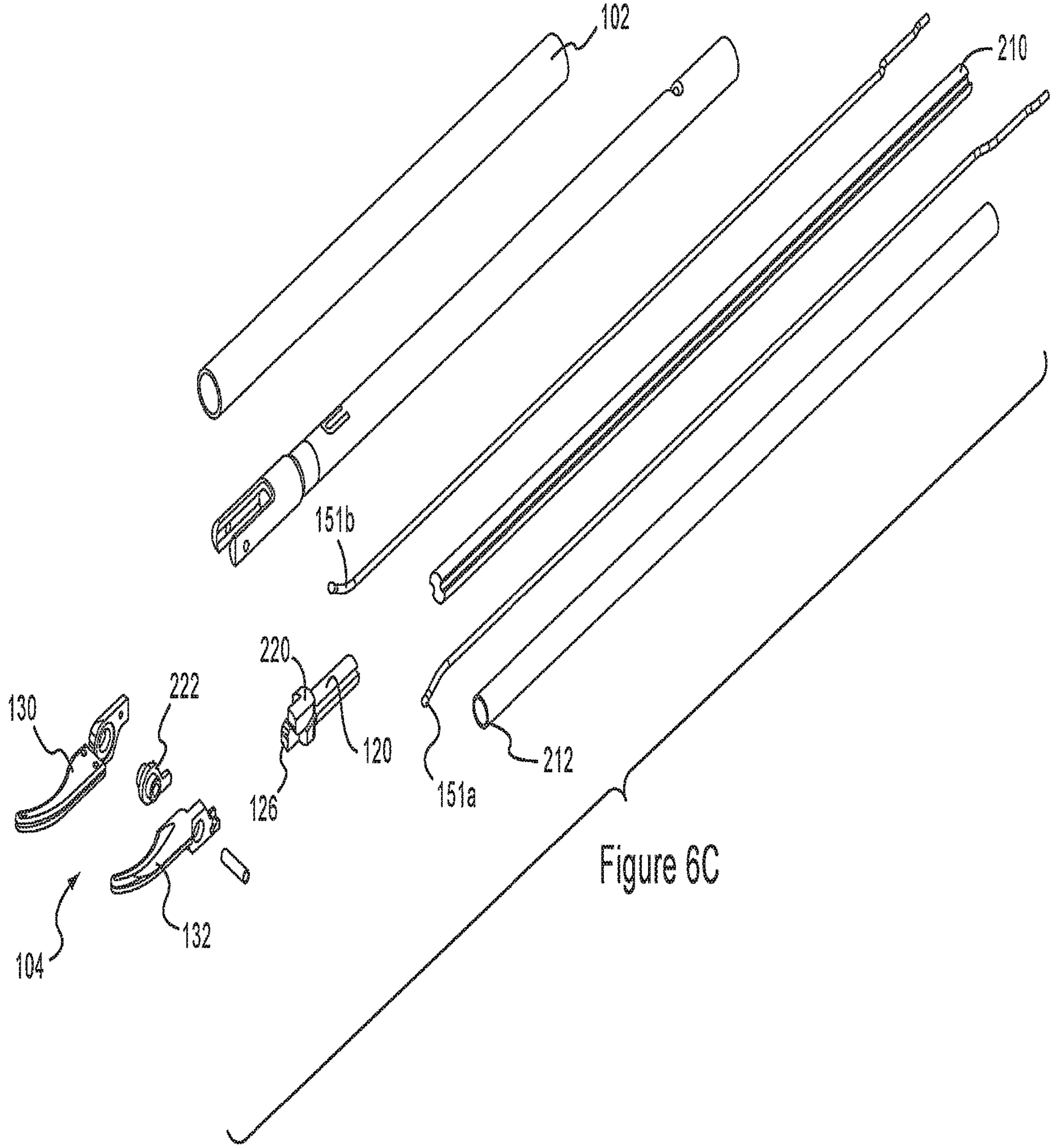
Figure 6D:
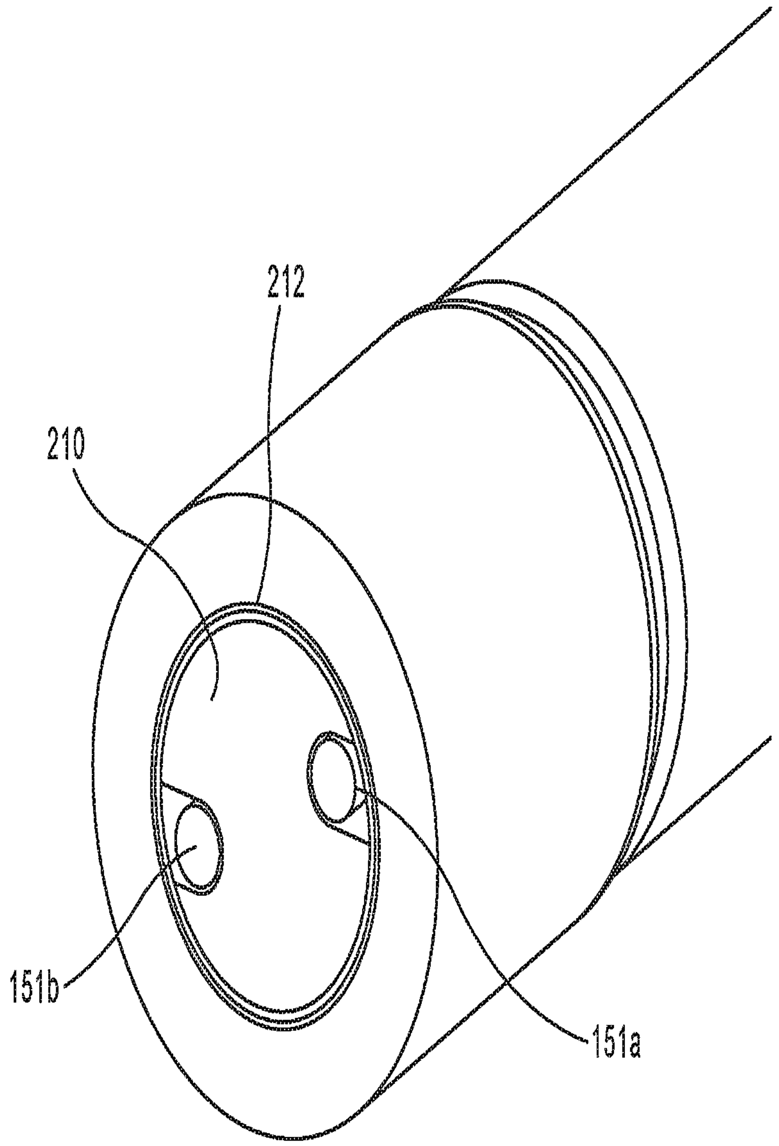
Figure 6E:
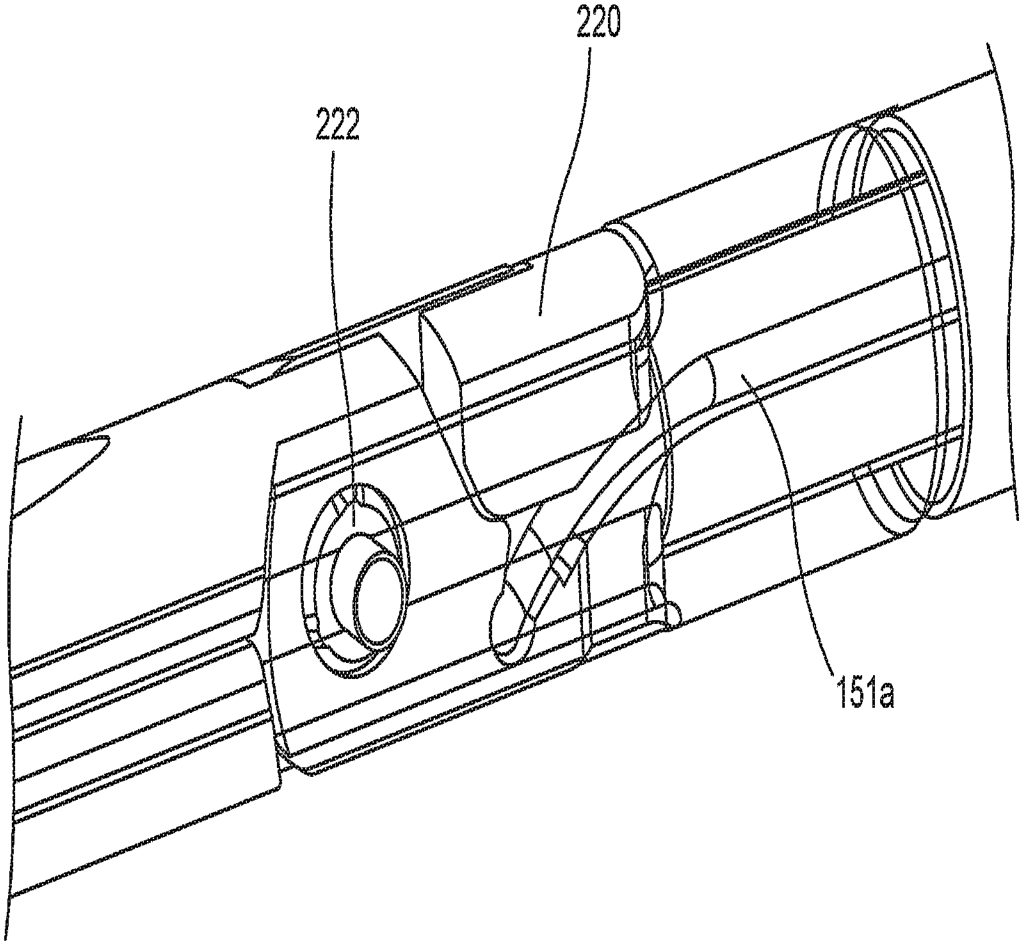

FIGS. 6C and 6E shows how actuator cables 151*a* and 151*b* are separated by insulator 220, and how jaw portions 130 and 132 are separated by insulator 222. Extrusion 210 and insulator 220 (with jacket 212 enclosing the tracks on the outside) guide the actuator cables to allow them to be pushed as well as pulled. The constrained track allows the assembly to push a flexible cable in order to open the jaw portions 130 and 132.

Located on an interior surface of grasper portion 130 are a series of non-conductive raised elements 134*a*, 134*b*, and 134*c* that ensure that the interior conductive surfaces of grasper portions 130 and 132 do not physically touch and are maintained at a constant and predictable separation distance from each other when the grasper portions 130 and 132 are in a closed position. Raised elements 134*a*, 134*b* and 134*c* may be on either of the interior surfaces of grasper portions 130 or 132.

In other embodiments, non-conductive elements 134*a*, 134*b* and 134*c* may be made of a variety of non-conductive material. For example the non-conductive elements may be made of a ceramic material, nylon, polystryenes, Nylons, Syndiotacticpolystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

Handle portion 108 includes an exterior shell portion 144 that forms part of a casing that surrounds several of the components within electrical connection and linkage system 118. A second portion of the casing is indicated as reference number 146. Casing portion 146 connects to thumb lever 110. Enclosed in a top portion of casing portion 146 are a shaft collar 148, a cable collar 150, and a ring cable collar 154 that serve to actively engage the shaft assembly 102 with the overall handle assembly 118. Cable assembly 116 is coupled with a flex circuit 142. A length of cable 140 extends from the cable assembly 116 and is coiled about cable collar 150 in order to allow the shaft assembly 102 to rotate freely without undue resistance to the user. Rotational element 114 couples to the housing portions 144 and 146 and allow a user to rotate the shaft assembly 102 and alter the presentation of the end effector 104 during a procedure.

Various fastening devices secure the components of the handle assembly together such as screws 158, 160, 162, and 164 as well as pin 156. Alternatively, sonic welding or other connection techniques may be utilized to secure the components together. Switch 152 engages with the thumb lever 110 and is adapted to engage the power delivery through cable assembly 116 as delivered from an electrosurgical generator.

FIGS. 6A-6C show the components that form the electrical connection between a power source, such as a radio frequency electrosurgical generator, and the device 100, eventually delivering the electrosurgical energy to the end effector 104. The connector 170 is keyed for insertion into the output of an electrosurgical generator (See e.g. FIG. 7). The connector 170 is coupled to the cable assembly 116. The length of the cable assembly 116 is determined by the particular application but is preferably long enough to allow operation of the instrument at a position remote from the electrosurgical generator. At an end of the cable assembly 116 opposite the connector 170, a strain relief device 180 is intermediate with an exit portion 190 of the cable assembly 116.

The cable assembly 116 houses four conductors, 182, 184, 186, and 188. In general the four conductors provide the RF power 182 and 184 to the end effector 104 a common/ground conductor 186 and a switch conductor 188 that couples with an identification resistor that signals the general as to what type of device is plugged in to the power source.

Figure 7:
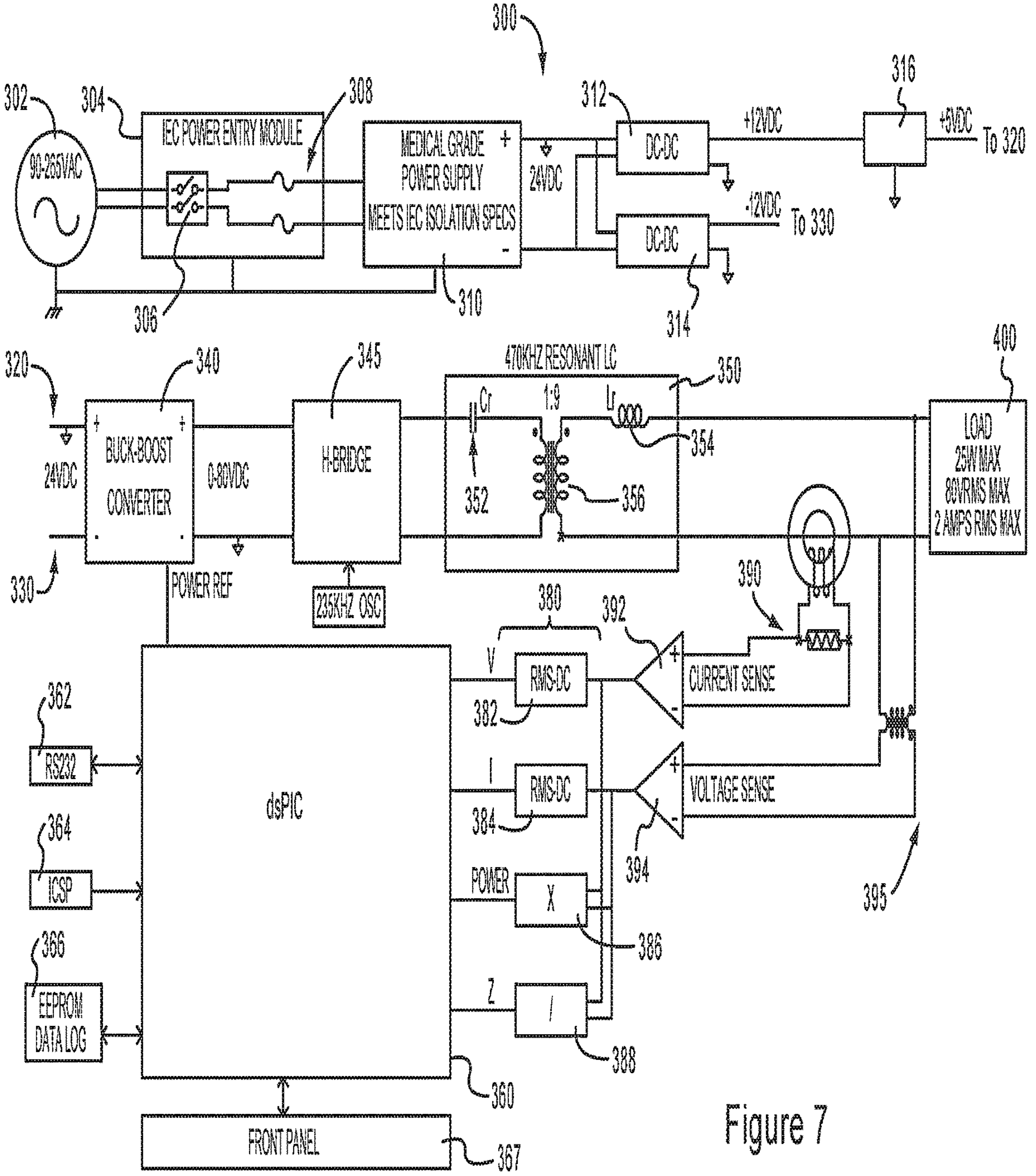
FIG. 7 is a block diagram of an RF power generator system in accordance with aspects of the present invention.

With reference to FIG. 7, a schematic of an RF generator 300 is shown. The use of an RF generator in connection with the delivery of electrosurgical energy is generally known in the art. However, aspects described herein that relate to the functioning and sequencing of low-power and energy delivery has not been described before.

Generator 300 inputs AC power from a wall outlet 302 and delivers that AC power to a power module 304 such as an IEC power entry module. Power module 304 may include such components as a DPDT switch 306 and 2 replaceable fuses 308. Power is transferred from power module 304 to a power supply unit 310. Preferably in connection with medical applications the power supply unit 310 is a medical grade power supply such as a CSS65-24 from Lambda. DC to DC converters 312 and 314 convert a 24 volt output of the power supply 310 into a pair of 12 volt outputs that are used to power control circuits. Power supply 310 then serves as the inputs 320 and 330 to a Buck-Boost Converter 340. The output of the converter 340 is passed to an H-Bridge circuit 345 which then passes that signal to a resonant LC transformer circuit 350. The transformer circuit 350 includes capacitor 352, inductor 354 and transformer 356. In one embodiment, transformer 356 is a 1:9 transformer. From the transformer 356, power is delivered to a load 400. In one embodiment, load 400 is a grasper/sealer instrument 100 as described above in connection with FIGS. 1-6 and the power delivered to instrument 100 is no more than 25 Watts, no more than 80 Volts RMS, and less than 2 Amps RMS.

Controller 360, in conjunction with the components described below, is used to sense various aspects of the energy applied to load 400, and adjust one or more of the energy characteristics in response to the vessel sealing process. Coupled to the load 400 (e.g. an electrosurgical instrument) are a current sensor circuit 390 and a voltage sensor circuit 395. Based on the sensed current and voltage, op-amps 392 and 394 pass these values to conversion circuits 380 that includes voltage RMS-DC Converter 382 and a current RMS-DC Converter 384. A multiplier 386 and a divider 388 derive power and impedance respectively from the sensed voltage and current. Each of the circuits 382, 384, 386 and 388 provide input data to the controller 360 which can then process and analyze the various input to indicate the state of the vessel sealing process. These circuits 382, 384, 386 and 388 also may be used as direct feedback signals to the Buck-Boost converter controller.

In some embodiment a user input panel 368 may be included that allows operator interaction with the controller and may include a display and some form of input device (such as a keyboard, mouse, pointer, dials or buttons). Data from the controller 360 may be output via analog or digital means such as an RS-232 connector 362, programming port 364 or memory chip 366.

Figure 8:
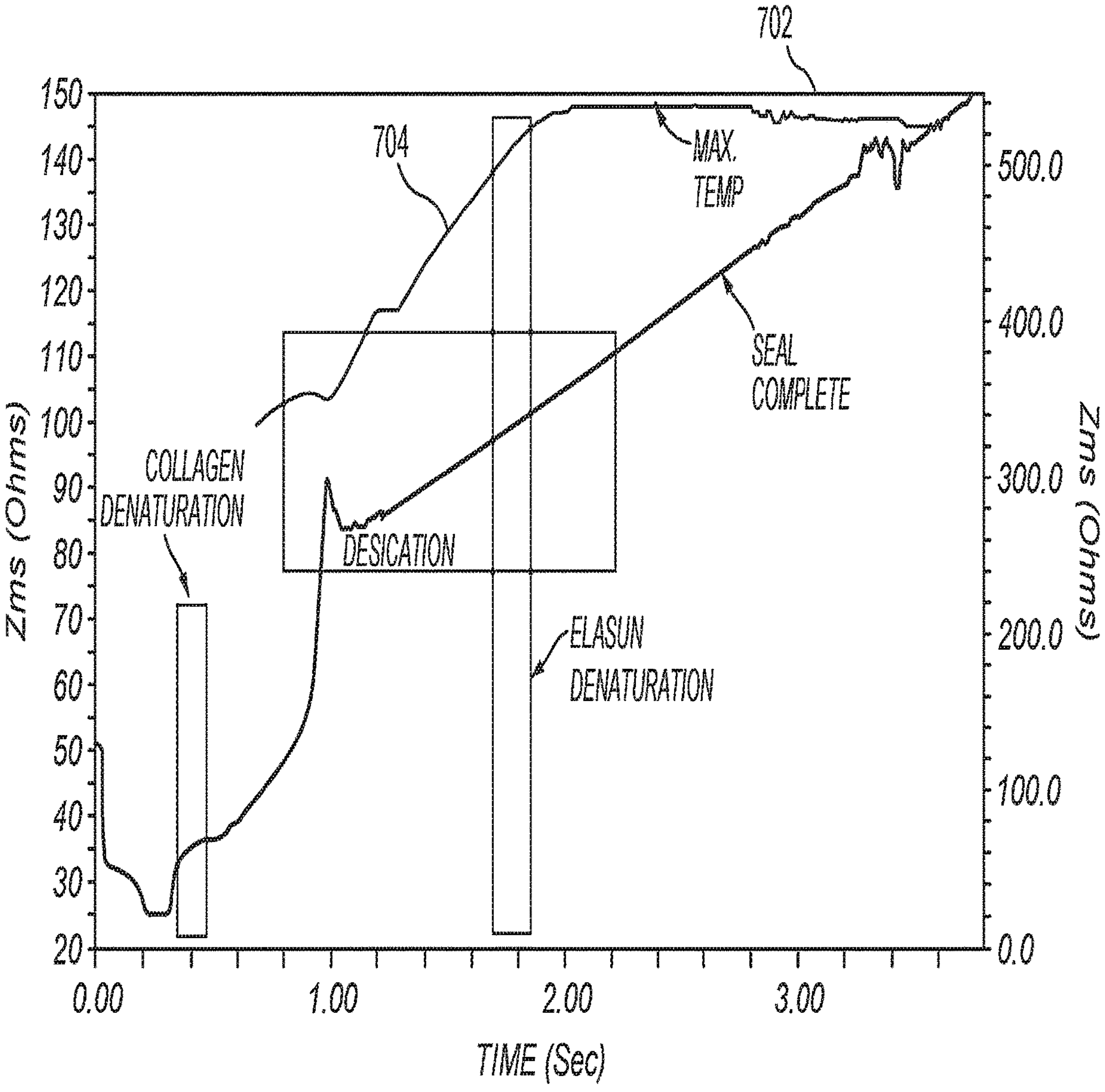
FIG. 8 is a prior art vessel sealing impedance curve.

FIG. 8, shows a known impedance curve as applied to RF vessel sealing and shows the changing impedance of a vessel and the various phases the vessel impedance goes through during an RF electrosurgical sealing process. In FIG. 8, the impedance is responding to changes in the power applied to the jaws of the surgical device. The tissue being sealed goes through several stages of change in order to achieve a complete seal. Prior systems effected vessel sealing by adjusting the power through the sealing cycle by pulsing the current and voltage applied to the tissue according to observing the rate of change of impedance during the rising section of the curve from the minimum value through the denaturation and desiccation and adjusting the power to the vessel in order to control that change. However, these systems cannot apply a uniform power delivery scheme that would apply to vessels of varying sizes.

Power Delivery Sequencing

Throughout the sealing process, the impedance of the vessel is calculated in real-time by measuring the voltage and current to the jaws. (Z=V/I). Since it is known that the impedance will follow the prescribed format, impedance thresholds can be set which act as trip points to cause the power profile curve to advance to the next phase of its settings. However, if the impedance limit is not met before the time has elapsed, the curve advances to the next phase. Each phase of the curve advances to the next phase according to an “OR” logic. If any one of the parameters is met according to impedance or time, the power profile is advanced.

In accordance with one aspect of the present invention it is desirable to achieve a single set of parameters that would be effective at sealing blood vessels with a diameter under 6 mm, typical in micro-surgery applications, pediatric patients, and surgical sites that are often difficult to reach and/or visualize.

Examples

The following examples are illustrative of aspects of the present invention but are not meant to be limiting under 35 U.S.C. § 112 of the United States Patent Laws, Article 123(2) of the European Patent Laws or any corresponding national country patent laws concerning the adequacy of the written description. By giving these examples, it is submitted that variations in the scope of the test results and corresponding implementations and claim scope are clearly and unambiguously disclosed to one of skill in the art.

Vessel Sealing Results

Table 1 shows the electrical characteristics associated with various seals performed according to aspects of the present invention.

TABLE 1

| Seal Number | Vessel Size (mm) | Power (W) | Peak Current (A) | Peak Voltage (Vrms) | Seal time (sec) | Burst Pressure (mm Hg) |
|---|---|---|---|---|---|---|
| 41-3 | 5 | 10 | | 80 | 1.3 | 687 |
| 41-4 | 5 | 10 | | 78 | 1.5 | 687 |
| 41-5 | 4 | 10 | 1.1 | 84 | 1.1 | 1034+ |
| 41-6 | 4 | 10 | 0.9 | 80 | 1.1 | 1034+ |
| 42-3 | 3.5 | 10 | 0.8 | 81 | 1.6 | 899 |

TABLE 1-continued

| Seal Number | Vessel Size (mm) | Power (W) | Peak Current (A) | Peak Voltage (Vrms) | Seal time (sec) | Burst Pressure (mm Hg) |
|---|---|---|---|---|---|---|
| 42-4 | 3.5 | 8 | 1.05 | 82 | 1.4 | 899 |
| 43-1 | 5 | 8 | 1 | 80 | 2.3 | 786 |
| 43-2 | 5 | 10 | 0.95 | 82 | 2.2 | 786 |
| 43-3 | 5 | 15 | 1 | 80 | 2.2 | 889 |
| 43-4 | 5 | 10 | 1 | 83 | 2.6 | 889 |
| 43-5 | 5 | 15 | 1 | 83 | 2.5 | 682 |
| 43-6 | 5 | 10 | 1 | 76 | 2.1 | 682 |
| 44-1 | 1.5 | 15 | 1 | 80 | 1.5 | 1034+ |
| 44-2 | 1.5 | 15 | 1 | 84 | 0.8 | 1034+ |
| 44-3 | 3 | 10 | 1 | 81 | 1.1 | 889 |
| 44-4 | 3 | 10 | 1.15 | 78 | 2.1 | 424 |
| 45-3 | 2 | 8 | | 78 | 1.5 | 584 |
| 45-4 | 2 | 15 | | 82 | 1.5 | 584 |
| 45-5 | 4 | 10 | | | 2 | 734 |
| 45-6 | 4 | 10 | 1.19 | 81 | 2.4 | 734 |
| 46-1 | 5 | 15 | | 78 | 1.25 | 780 |
| 46-2 | 5 | 15 | | 80 | 1.25 | 780 |
| 46-5 | 3.5 | 15 | | 78 | 3.5 | 682 |
| 46-6 | 3.5 | 15 | | 78 | 1.25 | 682 |
| 47-1 | 5 | 15 | 0.82 | 38 | 3 | 698 |
| 47-2 | 5 | 15 | 0.84 | 34 | 3 | 698 |
| 47-3 | 2.5 | 15 | | 81 | 1.5 | 589 |
| 47-4 | 2 | 15 | | 77 | 0.8 | 589 |
| 47-5 | 4.5 | 15 | 0.94 | 42 | 1.7 | 1034+ |
| 47-6 | 4.5 | 15 | | 78 | 1.7 | 1034+ |
| 48-1 | 2.5 | 10 | 0.9 | 80 | 0.5 | 424 |
| 48-2 | 2.5 | 10 | 1 | 80 | 1.2 | 424 |
| 48-3 | 3 | 10 | | 77 | 1.3 | 693 |
| 48-4 | 3 | 10 | 1.15 | 82 | 1.1 | 693 |
| 49-3 | 4 | 10 | 0.8 | 81 | 0.4 | 801 |
| 49-4 | 4 | 10 | 0.78 | 84 | 0.35 | 801 |
| 49-5 | 6 | 10 | 0.84 | 81 | 3 | 526 |
| 49-6 | 6 | 10 | 0.86 | 82 | 2.1 | 526 |
| 50-1 | 6 | 15 | 0.82 | 82 | 1.8 | 729 |
| 50-2 | 6 | 15 | 0.84 | 80 | 1.95 | 729 |
| 50-3 | 4 | 15 | 0.76 | 81 | 0.6 | 536 |
| 50-4 | 4 | 15 | 0.8 | 82 | 0.7 | 536 |
| 50-5 | 3 | 15 | 0.78 | 81 | 0.6 | 623 |
| 50-6 | 3 | 15 | 0.84 | 84 | 0.85 | 623 |
| 51-1 | 6 | 15 | | | | 708 |
| 51-2 | 6 | 15 | 0.72 | 79 | 1.3 | 708 |
| 51-3 | 3 | 15 | 0.86 | 82 | 1.2 | 1034+ |
| 51-4 | 3 | 15 | 0.84 | 81 | 0.8 | 1034+ |
| 51-5 | 2 | 15 | | | | 478 |
| 51-6 | 2 | 15 | 0.8 | 82 | 0.55 | 478 |
| 52-3 | 3 | 10 | 0.8 | | 1.25 | 1034+ |
| 52-4 | 3 | 10 | 0.78 | 81 | 0.4 | 1034+ |
| 52-5 | 2 | 15 | 0.88 | 80 | 0.85 | 532 |
| 52-6 | 2 | 10 | 0.92 | 81 | 0.9 | 532 |

With respect to the test results described in Table 1, the examples were completed by the power being held constant while current and voltage were allowed to float to the maximum values. The power was disengaged when Vmax reached 80 Volts RMS or Impedance reached 200 ohms. An initial cycle was established with a one (1) second ramp to maximum power followed by a two (2) second hold and then a one (1) second hold at a minimum power of 5 watts. If the power is left on too long, the additional power applied to the vessel will rapidly increase the impedance. In one embodiment it is envisioned that the power is deactivated within 100 msec. Complete and translucent seals were obtained at as low as 7 watts maximum power.

The time to Pmax for the series was 1 second. The observations were that 5 W did not provide an adequate seal and both 10 W and 15 W began to show charring of the vessel. It was found that translucency wasn't necessarily a good indication of a good seal. Burst tests of some clear seals did not achieve the desired 500 mm Hg (~10 psi level). It was found that some charring of the seals seemed to produce stronger seals that reach a 500 mm Hg burst strength. A series of 30 tests were then run where the time to Pmax was reduced to 0.5 seconds in order to reduce the total time of the seal and to get more energy into the vessel more quickly.

The time to Pmax was fixed at 0.5 seconds and the time to Pmin was fixed at 0.2 seconds. Pmax and Pmin were then incrementally adjusted to optimize the seal results. This testing established Pmax at 12 W and Pmin at 5 W, with Pmin being as low as 0 Watts as providing reasonable and consistent seals. Subsequent testing attempted to bracket the range for which good seals could be achieved. This ranged from 10 W to 14 W. In other embodiments the range for Pmax and Pmin is between 5 W to 10 W, alternatively between 2 W to 15 W.

In a second example, the goal was to enable seal times under 3 seconds. In this embodiment, power delivery of 12 watts for 1.1 seconds followed, by 5 watts for 1.5 seconds gave good results. These settings were initially set based on observations that seals at 7 W took about 3 seconds. If shorter sealing times were desired, it was understood that a higher power setting would be required since the seals are the result of the total energy delivered to the vessel.

Approximately 100 seals (See Table 1) were performed with varying results. The primary problem with obtaining repeatable seals at a constant power setting was that there was often arcing between the jaws and a subsequent burn-through of the vessel. In particular, tests performed using the parameters that worked on large vessels when applied to smaller vessels often had arcing at the end of the seal cycle. Experimentation realized that settings were not simply power and time dependent. Further testing incorporated the impedance threshold and voltage and current limits described below.

Figure 10:
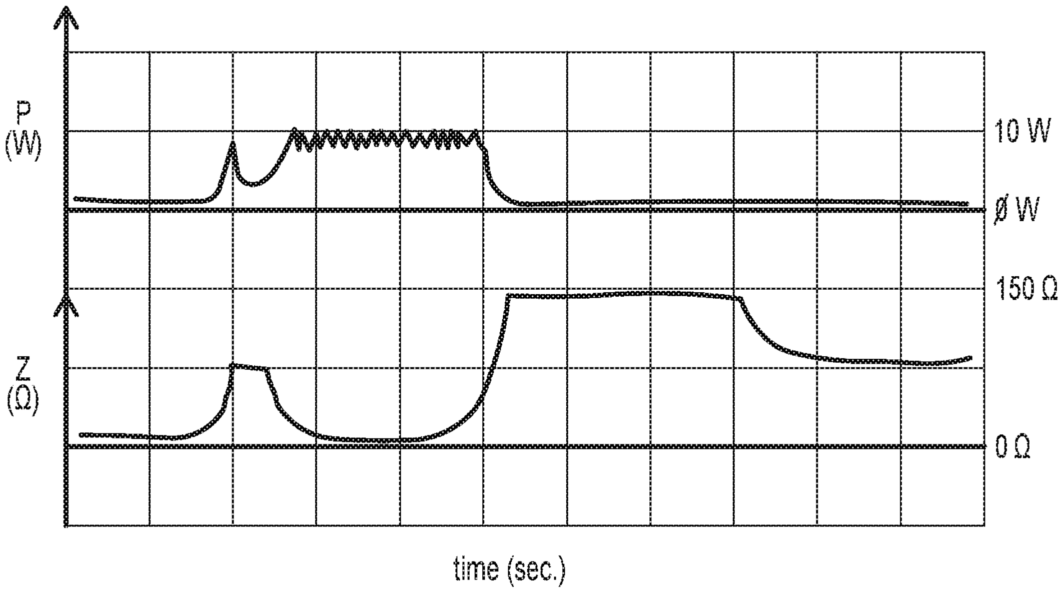
FIGS. 10-14 are oscilloscope traces of various vessel sealing procedures in accordance with aspects of the present invention.
Figure 11:
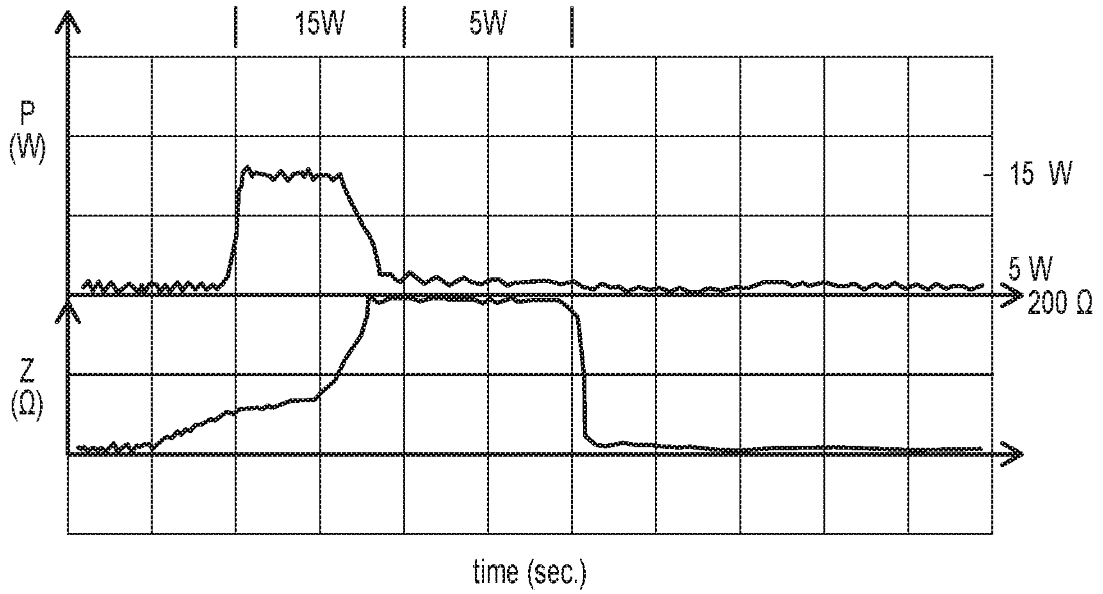

In another example seals were effected based on real-time measurements of the impedance. Examples of viable seals were created at 7 W peak power for 2.9 sec followed by 2 W of sustained minimum power. FIGS. 10 and 11 show the power output on an oscilloscope for these seals. The maximum output scale for the impedance on the user interface is 200 ohms. When the impedance reaches 200 ohms, the programmed input power curve switches to the next phase of the profile.

During the seals shown in FIG. 10, the maximum impedance was set to 175 ohms. This seal was following the typical bathtub shaped curve of impedance changes. The tissue begins to desiccate and the impedance drops. As it continues to dry out, the impedance begins a rapid rise. In this case, the impedance threshold was attained and the power was turned off.

CONCLUSIONS

Testing confirmed that controlled RF sealing of blood vessels can be achieved with as little as 7 Watts of power applied. Voltage and current applied during these seals were less than 50 volts and 0.6 A, respectively. The square area of the jaws used is 0.023 $in^2$/14.84 $mm^2$. The maximum current density applied by the system and as represented by I/A=0.6 Amps/14.84 $mm^2$ or 0.040 A/$mm^2$.

These tests and examples demonstrated that vessels up to 6 mm in size can be sealed with a low power RF energy output that utilizes a small bipolar grasper jaw end effector. Parameters of such a system include applied pressure, current density, low voltage, impedance monitor and midpoint. Steps for sealing may include one or more of the following:

a. Apply pressure to the tissue sufficient to compress the instrument jaws to less than or equal to 0.005". This pressure must also be high enough so that as the tissue contracts during heating, the jaws do not deflect and the gap between the jaws remains constant. Experimental data indicates that this pressure requirement is between 65-110 lb/in$^2$. In another embodiment the pressure requirement may be up to approximately 125 lb/in$^2$.

b. Radio frequency current is then applied to the tissue such that the current density is in the range of 0.034-0.1 Amps/mm$^2$. This current is sufficient to heat the tissue quickly so that the internal elastic laminae will fuse. A temperature of about 140° C. is required for this to occur.

c. Power delivery from the generator is generally less than 20 Watts to deliver this current density but may be as high as 35 Watts. Higher power may shorten the sealing time.

d. After the tissue begins to desiccate, the power may be reduced by 60-80% and heating is continued for a period of time before shutting off. The power can be reduced either when the tissue impedance reaches a level of 150-250 ohms or at a set time interval.

e. The voltage of the system is limited to less than 100 Volts RMS and peak voltage is typically in the range of 85 Volts RMS.

f. One or more wait states may also be interposed between the above steps.

Figure 9:
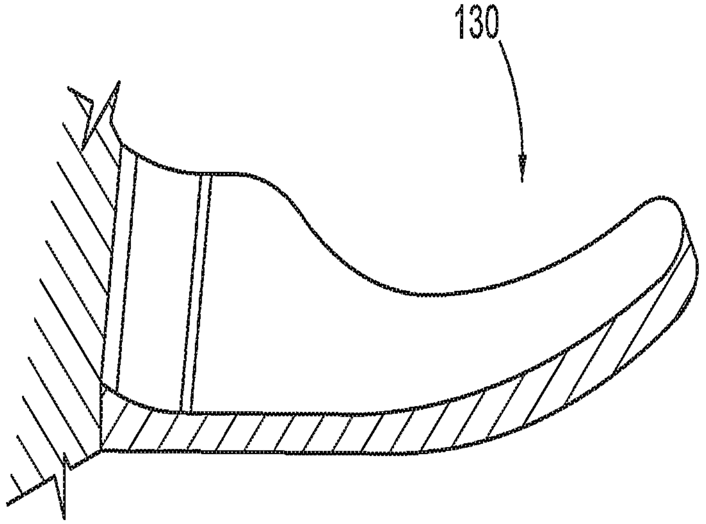
FIG. 9 is an end effector constructed in accordance with aspects of the present invention.

As demonstrated, vessel sealing is possible using a low power system by limiting jaw size and applying high pressure. A jaw of approximately 3 mm in width and 10-12 mm in length with a cross-sectional area of approximately 15-22 mm$^2$ is preferred but other geometries are contemplated. FIG. 9 shows one embodiment of an end effector jaw geometry, such as a Maryland style jaw, as used in connection with aspects of the present invention. When describing the surface area of the jaws in FIG. 9, reference is made to the surface area of the jaws that actually align with each other and grasp around the tissue being sealed. In some embodiments, there may be curved surfaces or tapered edges to the jaw surface that does not actually perform the bulk of the sealing function. When describing jaw surface area, it is not intended to encompass these portions of the jaw that are outside the normal boundaries of the sealing surface. In combination with the power delivery schemes described herein, the system results in a significantly reduced power requirement over standard bipolar sealing systems. Power requirements in some embodiments are in the range of 10-35 Watts.

In accordance with other testing aspects, non-conductive spacers, such as ceramic beads, were incorporated into the instruments to stop the jaws before they touch and prevent short circuits in the electrical systems. The ceramic beads also provided a means of keeping the jaws parallel since the moving jaw will land on the top of the beads.

In the testing environment, a silk suture material (0.006" diameter) that is non-conductive and will not melt during sealing was utilized to maintain the separation between jaw surfaces and prevent arcing. In the examples described in Table 1, two wraps of the suture were placed around the upper jaw so that the jaws would be separated by 0.006" when they were closed by the spring.

In accordance with another example, and with the non-conductive sutures in place, the power was set at 12 W as a nominal starting point and bracketed from 10 W to 14 W. When full jaw bites were sealed (100% filling of jaws with tissue), there were high quality seals, excellent translucency, with minimal sticking and charring. However, attempts to perform seals using these settings on smaller vessels that fill less (50-75%) of the jaw still resulted in arcing. Additional testing bracketed Pmax between 7 W and 15 W. Pmin was set at 5 W and bracketed between 4 W and 7 W. Since there was no control limit on parameters other than power and time, the lower power settings were used to produce reasonable seals on smaller vessels in the range of 50-80% jaw tissue fill. When the vessels filled 100% of the jaws, the 7 W was not sufficient to seal and a higher power near 12 W was necessary to adequately seal these larger vessels.

In accordance with other examples, further seals were provided by setting impedance thresholds in the user interface. It was then possible to set break points in the power curve that could limit the power delivered to the jaws by watching the real-time rise in impedance. Additional seals were performed with power and time as the sole modifiers of the power curve. An impedance trigger point added to the sequence and control of power delivery enabled the generator to quickly respond to changes in impedance and make the necessary adjustments.

Current and Voltage Clamping

In another aspect of testing the device, current and voltage limits were implemented. Based on observation, by limiting the voltage to 100 V arcing was eliminated in vessels ranging from 2 to 7 mm in width. These parameters made it possible to seal vessels that filled any percentage of the jaws thus the process and device were not limited to fully filling the jaws with tissue material. As an experimental validation, raising the voltage limit to 150 volts again caused arcing. This confirmed that the voltage limit is correctly stopping the arcing from occurring. The voltage maximum was set at between 75 and 100 volts for the next series of seals performed.

As another method to determine a maximum current for sealing, a system energy check was performed to see what current level is required to boil off saline that is placed between the jaws. It was found that 1.8 A was needed to cause the saline to begin to steam and boil away when RF power is applied to the jaws and this was used as the maximum current for sealing.

In another example, it was determined that a fast application of energy with a high influx of current creates good seals. Examples included following the high current energy with a one (1) second burst of low energy with Pmin set at 5 W.

In another example, a set of jaws 0.409 inches in length were installed in the system. The old jaws were removed and found to have experienced significant pitting due to the arcing incurred while there was no voltage limit in place. In addition to being longer than the original jaws, the top edges of the jaws were eased to reduce any sharp corner effects and high current concentrations that can occur with sharp edges.

In another example, seals were made with Vmax set to 75 volts and Imax set to 1.8 A. There were never any incidents of arcing observed in subsequent seals. Seals were created with the following set of parameters:

Pmax=15 W
Time at Pmax=2.5 sec
Pmin=5 W
Time at Pmin=1 sec
Vmax=75V
Imax=1.8 A
Time to Pmax=0.01
Time from Pmax to Pmin=0.01 sec A series of thirty-two (32) seals were performed on two animals. Vessels ranged from 2 mm to 6 mm wide. Twenty (20) of the 32 seals from the series were burst tested. All seals successfully withstood a minimum of 360 mm Hg. Seals were also successfully performed on mesentery tissue using the same settings.

Figure 12:
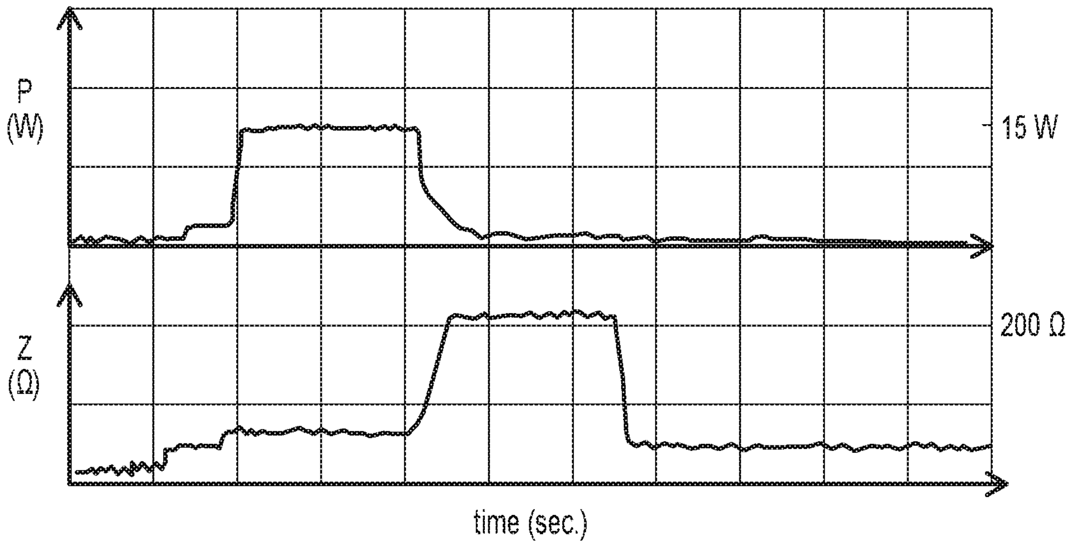
Figure 13:
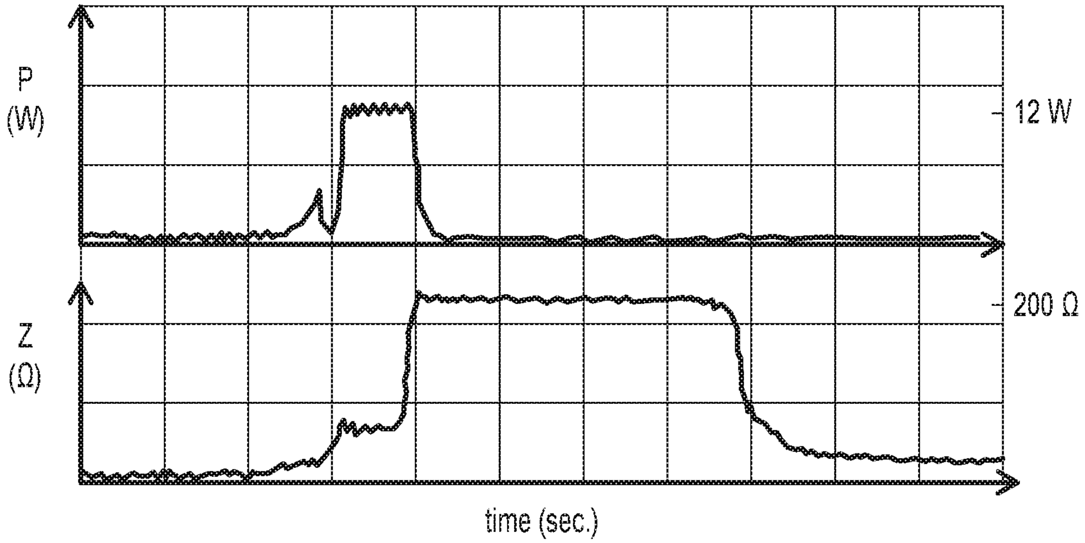

FIGS. 10-14 show reproductions of oscilloscope traces captured for three different seals demonstrating three different sizes of vessels. All were sealed using the above settings. All were set with the impedance threshold at 200 ohms. Seal time was determined by observing when the power was triggered to switch off. FIG. 11 shows the results for a 3.5 mm Vessel with a 1.5 second seal time. FIG. 12 shows the results for a 5 mm vessel with a 2.3 second seal time. FIG. 13 shows the results for a 1.5 mm Vessel with a 0.75 second seal time.

Figure 14:
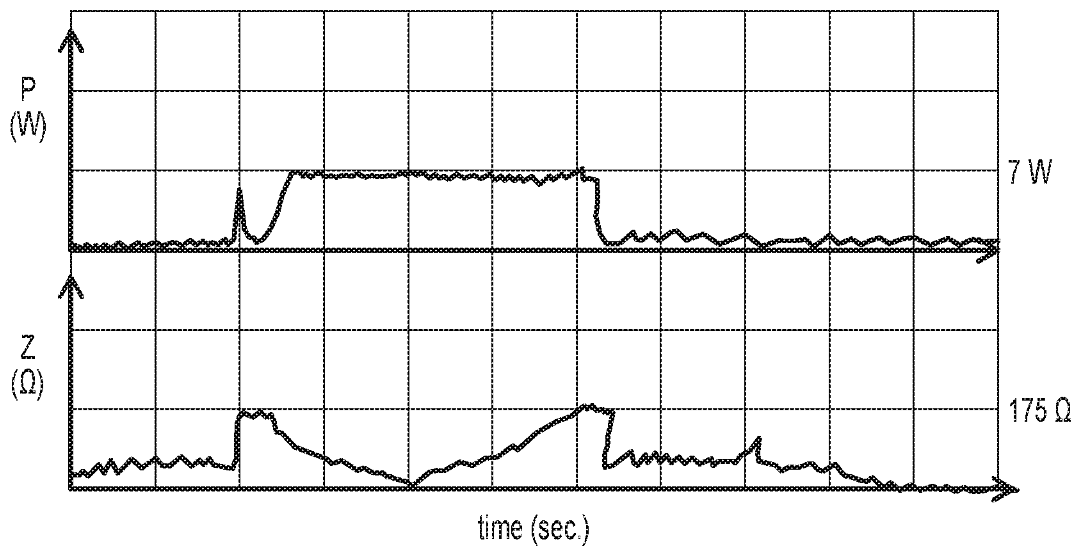

FIG. 14 shows a reproduction of an oscilloscope trace captured for additional sealing example where the maximum impedance was set to 175 ohms. This impedance of the seal followed the typical curve of impedance changes. Through the sealing process, the tissue begins to desiccate and the impedance drops. As it continues to dry out, the impedance begins a rapid rise. In this case, the impedance threshold was attained and the Pmax was switched to Pmin for the duration of the run.

Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention as expressed in the claims.

What is claimed is:

1. An electrosurgical generator, comprising:

a power supply configured for generating non-pulsing radiofrequency (RF) power having an output voltage, an output current and an output power; and control circuitry configured to provide automated controlled delivery of the non-pulsing RF power for a limited period of time to tissue being sealed by a tissue sealing device electrically connected to the generator, wherein the limited period of time begins upon a user activating delivery of the non-pulsing RF power to the tissue, and ends upon a determination by the control circuitry that the tissue has been fused, wherein the limited period of time is no greater than 5 seconds, and wherein the control circuitry is configured to hold the output power under 35 Watts throughout the limited period of time.

2. The electrosurgical generator of claim 1, wherein the tissue is a portion of a blood vessel.

3. The electrosurgical generator of claim 1, wherein the control circuitry is configured to hold the output power constant.

4. The electrosurgical generator of claim 1, wherein the control circuitry is configured to limit the output current to no more than 2 Amperes RMS throughout the limited period of time.

5. The electrosurgical generator of claim 1, wherein the control circuitry is configured to limit the output voltage to no more than 100 Volts RMS throughout the limited period of time.

6. An electrosurgical vessel sealing system including the electrosurgical generator of claim 1, the system further comprising the tissue sealing device, wherein the tissue sealing device comprises a conductive sealing surface, and wherein the control circuitry is configured to deliver the non-pulsing RF power to the tissue being sealed at a current density that is not greater than 0.1 Amperes root mean square (RMS) per square millimeter of the sealing surface.

7. The electrosurgical generator of claim 1, wherein the control circuitry is configured to hold the non-pulsing RF power under a first maximum power when the impedance of the tissue is less than an impedance threshold, and to hold the non-pulsing RF power under a second maximum power lower than the first maximum power when the impedance of the tissue is greater than the threshold impedance, and wherein the second maximum power is between 60% to 80% of the first maximum power.

8. An electrosurgical generator, comprising:

a power supply configured for generating non-pulsing radiofrequency (RF) power having an output voltage, an output current and an output power; and control circuitry configured to provide automated controlled delivery of the non-pulsing RF power for a limited period of time to tissue being sealed by a tissue sealing device electrically connected to the generator, wherein the limited period of time begins upon a user activating delivery of the non-pulsing RF power to the tissue, and ends upon fusing of the tissue, and wherein the control circuitry is configured to hold the output current to no more than 2 Amperes root mean square (RMS), and to hold the output voltage under 100 Volts RMS, respectively, throughout the limited period of time.

9. The electrosurgical generator of claim 8, wherein the tissue is a portion of a blood vessel.

10. An electrosurgical vessel sealing system including the electrosurgical generator of claim 8, the system further comprising the tissue sealing device, wherein the tissue sealing device comprises a conductive sealing surface, and wherein the control circuitry is configured to deliver the non-pulsing RF power to the tissue being sealed at a current density that is not greater than 0.1 Amperes RMS per square millimeter of the sealing surface.

11. The electrosurgical generator of claim 8, wherein the control circuitry is configured to hold the output power constant.

12. The electrosurgical generator of claim 8, wherein the control circuitry is configured to hold the non-pulsing RF power under a first maximum power when the impedance of the tissue is less than an impedance threshold, and to hold the non-pulsing RF power under a second maximum power lower than the first maximum power when the impedance of the tissue is greater than the threshold impedance, and wherein the second maximum power is between 60% to 80% of the first maximum power.

13. The electrosurgical generator of claim 8, wherein fusing of the tissue is determined by the control circuitry.

* * * * *